(12) United States Patent
Masuda et al.

(10) Patent No.: US 9,091,005 B2
(45) Date of Patent: Jul. 28, 2015

(54) NONWOVEN WEB FOR FASTENER FEMALE MEMBER

(75) Inventors: Kazuhiko Masuda, Chiba (JP); Hisashi Morimoto, Ichihara (JP); Thomas Alexander Horn, Hofheim (DE); Mark James Kline, Okeana, OH (US)

(73) Assignee: MITSUI CHEMICALS, INC., Tokyo (JP)

( * ) Notice: Subject to any disclaimer, the term of this patent is extended or adjusted under 35 U.S.C. 154(b) by 721 days.

(21) Appl. No.: 11/678,282

(22) Filed: Feb. 23, 2007

(65) Prior Publication Data

US 2007/0275622 A1    Nov. 29, 2007

Related U.S. Application Data

(60) Provisional application No. 60/776,309, filed on Feb. 24, 2006, provisional application No. 60/776,455, filed on Feb. 24, 2006.

(51) Int. Cl.

| | |
|---|---|
| *A61F 13/62* | (2006.01) |
| *D04H 1/541* | (2012.01) |
| *D04H 1/4291* | (2012.01) |
| *D04H 3/007* | (2012.01) |
| *D04H 3/02* | (2006.01) |
| *D04H 3/147* | (2012.01) |
| *D04H 1/44* | (2006.01) |
| *D04H 13/00* | (2006.01) |

(52) U.S. Cl.
CPC *D04H 1/44* (2013.01); *A61F 13/62* (2013.01); *D04H 13/00* (2013.01); *Y10T 24/2733* (2015.01); *Y10T 24/2758* (2015.01); *Y10T 24/2792* (2015.01); *Y10T 428/2457* (2015.01); *Y10T 428/24355* (2015.01)

(58) Field of Classification Search
None
See application file for complete search history.

(56) References Cited

U.S. PATENT DOCUMENTS

| 3,727,615 A | 4/1973 | Duchane |
| 3,860,003 A | 1/1975 | Buell |
| 3,911,173 A | 10/1975 | Sprague, Jr. |
| 3,929,135 A | 12/1975 | Thompson |

(Continued)

FOREIGN PATENT DOCUMENTS

| EP | 0381087 | 8/1990 |
| EP | 0726977 | 8/1996 |

(Continued)

OTHER PUBLICATIONS

Japanese Office Action Issued in connection with the corresponding application No. 2012-089222 dated May 21, 2013.

(Continued)

*Primary Examiner* — Frank D Ducheneaux
(74) *Attorney, Agent, or Firm* — Rankin Hill & Clark LLP

(57) ABSTRACT

A nonwoven web is provided. The nonwoven web contains a side-by-side composite fiber having crimps. The composite fiber contains first and second propylene polymers. The nonwoven web contains a bonded portion that contains a bonding pattern containing zigzag unit patterns. The zigzag unit patterns are continuous and substantially parallel with a first direction and are disposed in a second direction at predetermined intervals. A triangle formed by adjacent three contact points of a first diagonal line and a second diagonal line of the unit pattern contains a part of the unit pattern that is adjacent to the triangle in the second direction.

22 Claims, 24 Drawing Sheets

(56) References Cited

U.S. PATENT DOCUMENTS

| | | | |
|---|---|---|---|
| 4,324,246 A | 4/1982 | Mullane et al. | |
| 4,342,314 A | 8/1982 | Radel et al. | |
| 4,463,045 A | 7/1984 | Ahr et al. | |
| 4,515,595 A | 5/1985 | Kievit et al. | |
| 4,573,986 A | 3/1986 | Minetola et al. | |
| 4,609,518 A | 9/1986 | Curro et al. | |
| 4,610,678 A | 9/1986 | Weisman et al. | |
| 4,629,643 A | 12/1986 | Curro et al. | |
| 4,673,402 A | 6/1987 | Weisman et al. | |
| 4,695,278 A | 9/1987 | Lawson | |
| 4,785,996 A | 11/1988 | Ziecker et al. | |
| 4,834,735 A | 5/1989 | Alemany et al. | |
| 4,842,666 A | 6/1989 | Werenicz | |
| 4,888,231 A | 12/1989 | Angstadt | |
| 4,892,536 A | 1/1990 | DesMarais et al. | |
| 4,902,738 A * | 2/1990 | Mitsuno et al. | 524/525 |
| 4,909,803 A | 3/1990 | Aziz et al. | |
| 4,940,464 A | 7/1990 | Van Gompel et al. | |
| 4,968,312 A | 11/1990 | Khan | |
| 4,990,147 A | 2/1991 | Freeland | |
| 5,006,394 A | 4/1991 | Baird | |
| 5,037,416 A | 8/1991 | Allen et al. | |
| 5,062,840 A | 11/1991 | Holt et al. | |
| 5,092,861 A | 3/1992 | Nomura et al. | |
| 5,137,537 A | 8/1992 | Herron et al. | |
| 5,147,345 A | 9/1992 | Young et al. | |
| 5,151,092 A | 9/1992 | Buell et al. | |
| 5,171,236 A | 12/1992 | Dreier et al. | |
| 5,221,274 A | 6/1993 | Buell et al. | |
| 5,246,433 A | 9/1993 | Hasse et al. | |
| 5,260,345 A | 11/1993 | DesMarais et al. | |
| 5,269,755 A | 12/1993 | Bodicky | |
| 5,269,775 A | 12/1993 | Freeland et al. | |
| 5,306,266 A | 4/1994 | Freeland | |
| 5,326,612 A | 7/1994 | Goulait | |
| 5,342,338 A | 8/1994 | Roe | |
| 5,382,400 A * | 1/1995 | Pike et al. | 264/168 |
| 5,387,207 A | 2/1995 | Dyer et al. | |
| 5,397,318 A | 3/1995 | Dreier | |
| 5,460,622 A | 10/1995 | Dragoo et al. | |
| 5,514,121 A | 5/1996 | Roe et al. | |
| 5,518,801 A | 5/1996 | Chappell et al. | |
| 5,540,671 A | 7/1996 | Dreier | |
| 5,554,142 A | 9/1996 | Dreier et al. | |
| 5,554,435 A * | 9/1996 | Gupta et al. | 442/346 |
| 5,569,234 A | 10/1996 | Buell et al. | |
| 5,571,096 A | 11/1996 | Dobrin et al. | |
| 5,607,760 A | 3/1997 | Roe | |
| 5,609,587 A | 3/1997 | Roe | |
| 5,625,222 A | 4/1997 | Yoneda et al. | |
| 5,635,191 A | 6/1997 | Roe et al. | |
| 5,643,588 A | 7/1997 | Roe et al. | |
| 5,653,703 A | 8/1997 | Roe et al. | |
| 5,669,900 A | 9/1997 | Bullwinkel et al. | |
| 5,858,515 A | 1/1999 | Stokes et al. | |
| 5,865,823 A | 2/1999 | Curro | |
| 5,897,545 A | 4/1999 | Kline et al. | |
| 5,938,648 A | 8/1999 | LaVon et al. | |
| 5,941,864 A | 8/1999 | Roe | |
| 5,945,193 A | 8/1999 | Pollard et al. | |
| 5,957,908 A | 9/1999 | Kline et al. | |
| 5,964,742 A | 10/1999 | McCormack et al. | |
| 5,968,025 A | 10/1999 | Roe et al. | |
| 5,977,430 A | 11/1999 | Roe et al. | |
| 5,997,520 A | 12/1999 | Ahr et al. | |
| 6,013,063 A | 1/2000 | Roe et al. | |
| 6,013,349 A * | 1/2000 | Takeuchi et al. | 428/152 |
| 6,054,202 A * | 4/2000 | Takeuchi et al. | 428/167 |
| 6,120,487 A | 9/2000 | Ashton | |
| 6,120,489 A | 9/2000 | Johnson et al. | |
| 6,140,551 A * | 10/2000 | Niemeyer et al. | 604/367 |
| 6,168,584 B1 | 1/2001 | Allen et al. | |
| 6,168,858 B1 * | 1/2001 | Hasegawa et al. | 428/315.5 |
| 6,680,422 B2 | 1/2004 | Roe | |
| 6,716,441 B1 | 4/2004 | Osborne et al. | |
| 6,770,065 B1 | 8/2004 | Sasaki et al. | |
| 7,244,497 B2 * | 7/2007 | Hartmann et al. | 428/373 |
| 2002/0029026 A1 | 3/2002 | Furuya et al. | |
| 2003/0077430 A1 | 4/2003 | Grimm et al. | |
| 2003/0176132 A1 * | 9/2003 | Moriyasu et al. | 442/361 |
| 2003/0233082 A1 | 12/2003 | Kline et al. | |
| 2004/0015144 A1 | 1/2004 | Mori et al. | |
| 2004/0067709 A1 * | 4/2004 | Kishine et al. | 442/327 |
| 2005/0009173 A1 | 1/2005 | Amand | |
| 2005/0027267 A1 | 2/2005 | Dyke et al. | |
| 2005/0125877 A1 | 6/2005 | Benjamin et al. | |
| 2005/0125923 A1 | 6/2005 | Benjamin et al. | |
| 2005/0129743 A1 | 6/2005 | Benjamin et al. | |
| 2005/0258576 A1 * | 11/2005 | Forry et al. | 264/517 |
| 2007/0021022 A1 | 1/2007 | Kishine et al. | |
| 2010/0326580 A1 | 12/2010 | Mori et al. | |

FOREIGN PATENT DOCUMENTS

| | | |
|---|---|---|
| JP | 6-507800 | 9/1994 |
| JP | 07-197367 | 8/1995 |
| JP | 09-000317 | 1/1997 |
| JP | 10-121359 | 5/1998 |
| JP | 11-335960 | 12/1999 |
| JP | 2000-023715 | 1/2000 |
| JP | 2000-516482 | 12/2000 |
| JP | 2002-010807 | 1/2002 |
| JP | 2002-65740 | 3/2002 |
| JP | 2002-209936 | 7/2002 |
| JP | 2002-233404 | 8/2002 |
| JP | 2003-009912 | 1/2003 |
| JP | 2003-038213 | 2/2003 |
| JP | 2003-221772 | 8/2003 |
| JP | 2006-034872 | 2/2006 |
| JP | 2006-265782 | 10/2006 |
| WO | 9414395 | 7/1994 |
| WO | 9512702 | 5/1995 |
| WO | 9516746 | 6/1995 |
| WO | 9524173 | 9/1995 |
| WO | 02061192 | 8/2002 |

OTHER PUBLICATIONS

Communication from European Patent Office dated Oct. 20, 2014 issued in the corresponding European patent application No. 13155740.7.

* cited by examiner

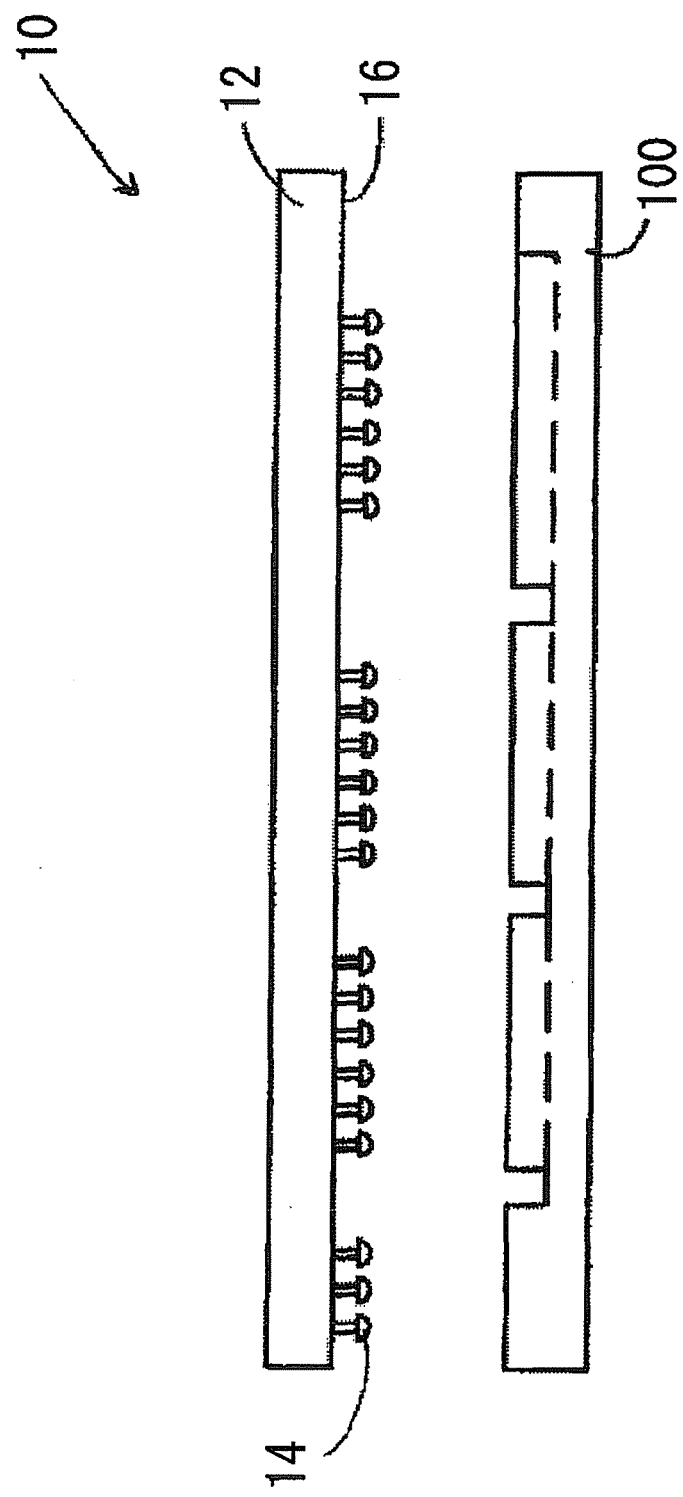

NONWOVEN WEB FOR FASTENER FEMALE MEMBER

RELATED APPLICATION

This application claims priority to U.S. Provisional Patent Applications 60/776,309 filed on Feb. 24, 2006, entitled A NONWOVEN FABRIC FOR FASTENER FEMALE MEMBER and 60/776,455 filed on Feb. 24, 2006, entitled A FASTENING SYSTEM, both of which are hereby incorporated by reference.

TECHNICAL FIELD

The subject invention generally relates to a nonwoven web for use in connection with a fastening system such as a receiving component of a fastener.

BACKGROUND ART

Refastenable mechanical fastening systems can be used in a wide number of applications. For example, such refastenable fastening systems can be used to connect one portion of a disposable absorbent article to another portion of the disposable absorbent article.

In general, mechanical fastening systems contain a receiving component (e.g., a female component) and an engaging component (e.g., a male component). In some mechanical fastening systems, the engaging component contains a plurality of hook elements, and the receiving component contains a plurality of loop elements. In a fastened state, the hook elements typically are entangled with the loop elements, thereby forming a connection between the engaging and receiving components.

Nonwoven webs can be used as the receiving component. Typically, a nonwoven receiving component contains a plurality of polymeric fibers. Portions of these fibers can be joined together by fiber-to-fiber bonds to form a web having sufficient available unbonded fibers or unbonded portions of bonded fibers and web integrity. The fiber-to-fiber bonds are typically formed by fusing portions fibers together via, for example, heat, pressure, or sound (e.g., ultrasonic) energy.

In some processes, a pair of heated calendering rolls can be used to create these fiber-to-fiber bonds. Typically, one of the calendering rolls contains a plurality of protrusions which extend outward from its outer surface. A constant force is generally applied to one of the calendering rolls such that as the nonwoven web passes between the calendering rolls, the protrusions apply pressure to the nonwoven web. In general, at the location of applied pressure, at least one fiber-to-fiber bond is created.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

One aspect of the subject invention provides a nonwoven web containing a bonded portion (e.g., embossed portion). The nonwoven web can be used as a receiving component/member of a fastener. The nonwoven web contains a composite fiber having crimps and containing first and second propylene polymers. The bonded portion contains zigzag unit patterns that are disposed in a machine direction at predetermined intervals, the zigzag unit patterns being continuous substantially parallel with a cross machine direction. A triangle formed by adjacent three contact points of a first diagonal line and a second diagonal line of the unit pattern contains a part of the unit pattern that is adjacent to the triangle in the machine direction.

To the accomplishment of the foregoing and related ends, the invention, then, contains the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 1A is an elevation view showing a fastening system that contains a nonwoven web in accordance with the subject invention.

DETAILED DESCRIPTION

Definitions

Figure 1B:
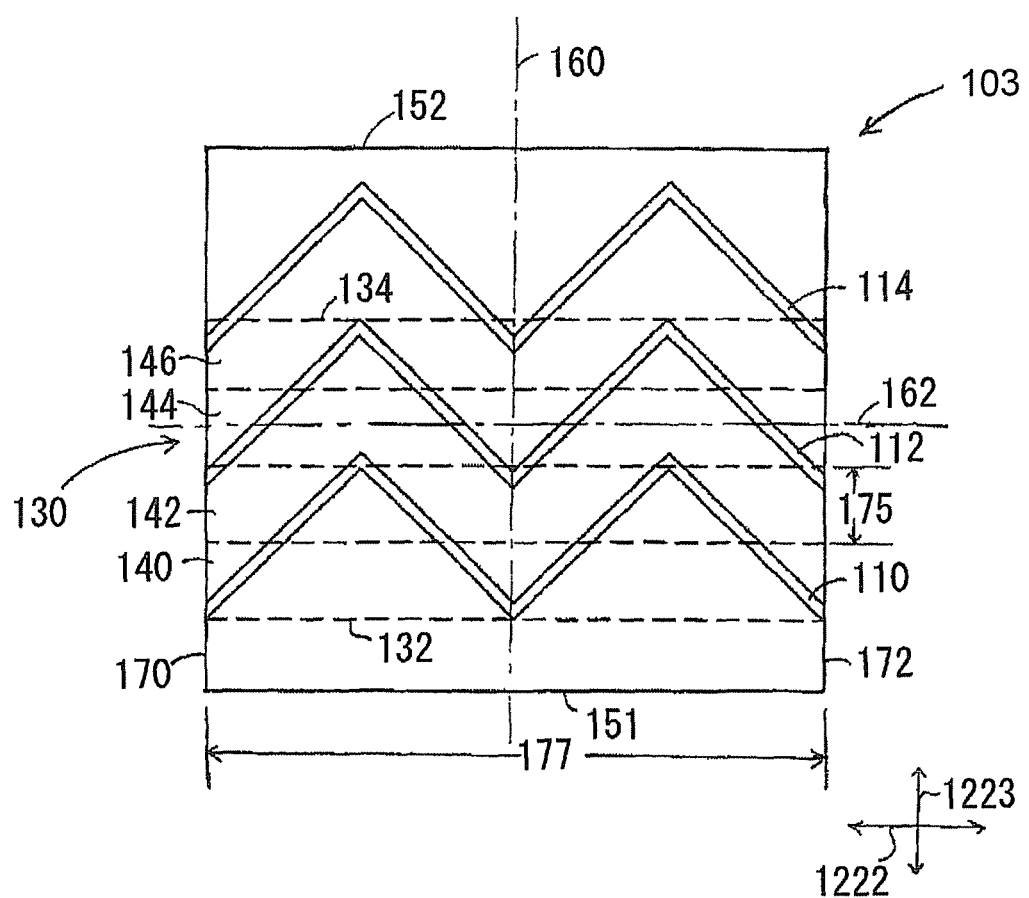
FIG. 1B is a plan view showing a receiving component of the fastening system of FIG. 1A, the receiving component containing a nonwoven web in accordance with the subject invention.

As used herein, the terms "absorbent article" and "article" refer to a wearable device that absorbs and/or contains liquid and, more specifically, refers to a device that is placed against or in proximity to the body of the wearer to absorb and contain the various exudates discharged from the body. Suitable examples include diapers, training pants, refastenable pants, pull-on garments, adult incontinence products and feminine care products such as sanitary napkins. Furthermore, the terms "absorbent article" and "article" include a "disposable absorbent article" which is intended to be discarded and not laundered or otherwise restored after no more than about ten uses, preferably after no more than about five uses, and most preferably after a single use (although certain components may be recycled, reused, or composted).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (e.g., element or surface is proximate to the wearer's garments that may be worn over the disposable absorbent article).

As used herein, the term "bond line" refers to a plurality of sites on a substrate where the fibers of the substrate have been fused together. The plurality of sites can be fused together to form the "line." However, the term "line," as used herein, can also describe a series of discrete points or short lines closely spaced so as to effectively approximate a line. Therefore, those skilled in art will recognize that although a solid line bonding pattern is described, the benefits of the subject invention can similarly be achieved by closely spaced points or discrete line segments which effectively approximate a line.

As used herein, the term "bond line pattern" refers to at least two bond lines which have some overlap between the at least two bond lines.

As used herein, the term "consecutive" means following one after another. For example, adjacent sweep regions of the subject invention may share boundaries with one another.

As used herein, the term "diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

As used herein, "elastically extensible" refers to characteristics of extensible materials that have the ability to return to approximately their original dimensions after a force that extended the extensible material is removed. Herein, any material or element described as "extensible" may also be "elastically extensible" unless otherwise provided.

As used herein, the term "joined" encompasses configurations whereby an element is directly secured to another element by affixing the element directly to the other element, and configurations whereby an element is indirectly secured to another element by affixing the element to an intermediate member(s) which in turn are affixed to the other element.

The term "longitudinal" is used herein to refer to a direction which is generally parallel to the longest edge of an element except where otherwise noted. In the context of disposable absorbent articles, a "longitudinal" direction runs substantially perpendicular from a waist edge to an opposing waist edge of the article and generally parallel to the maximum linear dimension of the article. Directions within ± about 45 degrees of the longitudinal direction are considered to be "longitudinal."

The term "lateral" refers to a direction running generally perpendicular to and in the same plane as the "longitudinal" direction. In the context of disposable absorbent articles, a "lateral" direction runs from one longitudinal edge of the article to an opposing longitudinal edge of the article. Directions within ± about 45 degrees of the lateral direction are considered to be "lateral."

The terms "machine direction" or "MD" refer to a direction which is generally parallel to the forward direction of a material, member, element, item, component, etc. through a process. For example, nonwovens are typically formed with a machine direction that corresponds to the long or rolled direction of fabrication. The machine direction can also be the primary direction of fiber orientation in the nonwoven.

The terms "cross machine direction" or "CD" refer to a direction which is generally perpendicular to and in the same plane as the machine direction.

The terms "pant," "training pant," "closed diaper," "prefastened diaper," and "pull-on diaper," as used herein, refer to disposable garments having a waist opening and leg openings designed for infant or adult wearers. A pant can be configured such that the pant has a closed waist and leg openings prior to being donned on the wearer, or the pant can be configured such that the waist is closed and the leg openings formed while on the wearer. A pant may be preformed by any suitable technique including, but not limited to, joining together portions of the article using a refastenable fastening system. A pant may be preformed anywhere along the circumference of the article (e.g., side fastened, front waist fastened, rear waist fastened). Examples of suitable pants are disclosed in U.S. Pat. No. 5,246,433; U.S. Pat. No. 5,569,234; U.S. Pat. No. 6,120,487; U.S. Pat. No. 6,120,489; U.S. Pat. No. 4,940,464; U.S. Pat. No. 5,092,861; U.S. Pat. No. 5,897,545; U.S. Pat. No. 5,957,908; and U.S. Patent Publication No. 2003/0233082 A1, all of which are hereby incorporated by reference in for this regard.

DESCRIPTION

In general, nonwoven webs which are to be used as receiving components are not completely bonded, e.g., not 100% fiber-to-fiber bonds. Because the fiber-to-fiber bonds typically render the bonded areas unengageable by an engaging component, bonding the nonwoven web completely can yield a poorly performing receiving component. Therefore, the protrusions extending outward from the outer surface of the calendering roll are typically spaced apart such that a particular bonding pattern is created in the nonwoven.

It may be desirable to have large, open, unbonded areas to assure that wherever a hook from the engaging component is placed an unbonded fiber or an unbonded portion of a bonded fiber is available to engage the hook. However, a bond pattern creating large, open, unbonded areas can have reduced strength in a cross machine direction because of the reduced number of fiber-to-fiber bonds in the unbonded areas. To compensate, some bond patterns can create fully enclosed areas e.g., fully bonded fibers surrounding unbonded fibers. However, a bond pattern which creates fully bonded fibers surrounding unbonded fibers can reduce the likelihood that a hook from an engaging component will find an unbonded fiber with which it can engage. Additionally, the bond pattern can negatively impact the quality of the fiber-to-fiber bonds. For, example because conventional bond patterns do not completely bond the nonwoven web, the pressure applied to the nonwoven web as the nonwoven web passes through the calendering rolls can fluctuate. In some cases, the pressure fluctuations can cause higher pressures at some fiber-to-fiber bond sites and cause lower pressures at other fiber-to-fiber bond sites. The higher pressure can result in overbonding or even cutting through fibers (which weakens the resulting web). The lower pressure may result in a reduced percentage of bonded area being formed compared to the desired percentage of bonded area, lower bond strength and/or lower bond quality. Additionally, the lower pressure may cause reduced strength in the cross machine direction.

Consequently, there is a need to provide a fastening system which includes a receiving component having a bond pattern which reduces the pressure fluctuations experienced by the receiving component during processing while maintaining sufficient areas of unbonded fibers and/or unbonded portions of bonded fibers.

A nonwoven web in accordance with the subject invention can be used for a receiving component (e.g., female component) of a fastener. The nonwoven web can have a sufficient fastening strength (e.g., peel strength, repeat peel strength, and tensile shear strength) and high mechanical strength in both of machine direction (MD) and cross machine direction (CD). The nonwoven web contains a bonded portion containing zigzag unit patterns that are disposed in a machine direction at predetermined intervals. The zigzag unit patterns are continuous generally parallel with the cross machine direction. It is believed that the nonwoven web has the sufficient repeat peel strength and mechanical strength in the CD because the adjacent unit patterns overlap each other in the MD by including a part of the adjacent unit pattern in an inside of a triangle formed by three adjacent contact points of a first diagonal line and second diagonal line.

In one embodiment, a receiving component containing the nonwoven web contains a first bond line, a second bond line, a bond zone, and a plurality of consecutive sweep regions. The first bond line and second bond line extend in a first direction, wherein the second bond line is disposed adjacent to the first bond line such that a portion of the second bond line overlaps a portion of the first bond line. The overlap is generally parallel to a second direction which is generally perpendicular to the first direction.

The bond zone circumscribes the first bond line and the second bond line. The plurality of consecutive sweep regions is disposed within the bond zone. Each sweep region extends in a direction generally parallel to the longitudinal axis, and each sweep region contains a length and a width. The lengths of the sweep regions are equal, and the widths of the sweep regions are equal. At least one sweep region contains a portion of both the first bond line and the second bond line, wherein the remaining sweep regions of the plurality of sweep regions contain at least a portion of the first bond line or at least a portion of the second bond line. Each sweep region has a bonded area, and the receiving component has a bond ratio between two sweep regions which is greater than or equal to about 1 and less than or equal to about 20.

A receiving component containing the nonwoven web can be employed for a fastening system. A mechanical fastening system typically contains an engaging component and receiving component. The engaging component contains a plurality of engaging elements. The receiving component has a longitudinal axis and a lateral axis, wherein the plurality of engaging elements are capable of engaging the receiving component.

Fastening systems containing the nonwoven web in accordance with the subject invention contain receiving components which can reduce the pressure fluctuations which can occur when producing the receiving component. Specifically, receiving components containing the nonwoven web in accordance with the subject invention contain a bond pattern which can reduce the pressure fluctuations experienced by the receiving component during processing. Additionally, a receiving component containing the nonwoven web in accordance with the subject invention can maintain a sufficient area of unbonded fibers and/or unbonded portions of bonded fibers such that the receiving component can be used with suitable engaging components in a fastening system.

The invention is now described with reference to the drawings, wherein like reference numerals are used to refer to like elements throughout. In the following description, for purposes of explanation, numerous specific details are set forth in order to provide a thorough understanding of the subject invention. It may be evident, however, that the invention can be practiced without these specific details. In other instances, well-known structures and devices are shown in block diagram form in order to facilitate describing the invention.

As shown in FIG. 1A, a fastening system 10 containing the nonwoven web in accordance with the subject invention may contain an engaging component 12 and a receiving component 100. The engaging component 12 may contain a plurality of hooks 14 which extend outward from an engaging surface 16. The receiving component 100 may contain a plurality of looped fibers (not shown) which are capable of becoming entangled with the plurality of hooks 14 of the engaging component 12. Examples of suitable engaging components are discussed hereafter.

The fastening system 10 can be utilized in a variety of consumer and commercial goods which may benefit from having the fastening system of the subject invention. Some examples of articles which can utilize the fastening system of the subject invention include disposable absorbent articles, body wraps, packaging, and industrial connections for abrasive pads, medical products, and the like.

As shown in FIG. 1B, the nonwoven web 103 that can be used for a receiving component may contain a plurality of bond lines, a bond zone 130, and a plurality of consecutive sweep regions. In some embodiments, the nonwoven web 103 may contain a first bond line 110, a second bond line 112, and a third bond line 114. Embodiments having more than three bond lines and less than three bond lines are contemplated.

The first bond line 110, in some embodiments, can be disposed adjacent to a first end edge 151 and the second bond line 112 can be disposed adjacent to the first bond line 110. The third bond line 114, in some embodiments, can be disposed adjacent to a second end edge 152 and adjacent the second bond line 112. In some embodiments, the first end edge 151 and the second end edge can extend from a first longitudinal edge 170 to a second longitudinal edge 172 in a direction generally parallel to a lateral axis 162.

As shown, in some embodiments, the first bond line 110, the second bond line 112, and the third bond line 114, can extend in a first direction 1222 from a first longitudinal edge 170 to a second longitudinal edge 172 of the receiving component 100. In some embodiments, the first direction 1222 can be generally parallel to the lateral axis 162. The first longitudinal edge 170 and the second longitudinal edge 172 can extend between the first end edge 151 and the second end edge 152 in a direction generally parallel to a longitudinal axis 160.

The nonwoven web 103 further contains the bond zone 130. The bond zone 130 circumscribes more than one bond line. For example, as shown, the bond zone 130 can circumscribe the first bond line 110 and the second bond line 112. The bond zone 130, in some embodiments, may contain a rectangle which contacts the outermost points of the first bond line 110 and the outermost points of the second bond line 112. In some embodiments, the outermost points of the first bond line 110 are those points on the first bond line 110 which are nearest the first end edge 151, nearest the first longitudinal edge 170, and nearest the second longitudinal edge 172. Similarly, in some embodiments, the outermost points of the second bond line 112 are those points on the second bond line 112 which are nearest the second end edge 152, the first longitudinal edge 170, and the second longitudinal edge 172. In some embodiments, the third bond line 114 can overlap into the bond zone 130 adjacent a second boundary 134 of the bond zone 130. In some embodiments, additional bond lines may overlap into the bond zone 130 either adjacent to a first boundary 132 or adjacent to the second boundary 134.

A plurality of consecutive sweep regions 140, 142, 144, and 146, can be disposed within the bond zone 130. A sweep region contains a portion of the receiving component 100 and is used to analyze the bonded area and total area of the portion of the nonwoven web 103 within that sweep region. An advantage of sweep regions with smaller lengths 175 is that essentially more data points on the bond lines can be collected. The higher number of data points can increase the accuracy of the calculation of the variability in the bonded area in the nonwoven web 103.

Each sweep region 140, 142, 144, and 146, contains a portion of the first bond line 110 and/or the second bond line 112. In some embodiments, some of the consecutive sweep regions 140, 142, 144, and 146, may contain portions of additional bond lines which overlap into the bond zone 130 either adjacent to the first end edge 151 or the second end edge 152. For example, because the third bond line 114 overlaps the bond zone 130, the sweep region 146 may further contain a portion of the third bond line 114.

At least one sweep region contains a portion of both the first bond line 110 and the second bond line 112. For example, as shown, in some embodiments, two sweep regions, e.g., 142 and 144, contain a portion of the first bond line 110 and the second bond line 112. Depending on the sizes of the sweep regions, one or more sweep regions may contain portions of more than one bond line. Embodiments containing more than four sweep regions and fewer than four sweep regions are contemplated.

Because the sweep regions 140, 142, 144, and 146, are consecutive, each sweep region shares a boundary with an adjacent sweep region. For example, sweep region 140 shares a boundary with sweep region 142. Similarly, sweep region 144 shares a boundary with sweep region 142. However, the sweep regions 140, 142, 144, and 146, are arranged such that the odd (first and third) sweep region, e.g., 140 and 144 do not share a boundary. Additionally, the sweep regions 140, 142, 144, and 146, are arranged such that the even (second and fourth) sweep regions, e.g., 142 and 146, do not share a boundary.

The consecutive sweep regions 140, 142, 144, and 146, are rectangular and extend from the first longitudinal edge 170 to the second longitudinal edge 172 of the nonwoven web 103. The consecutive sweep regions 140, 142, 144, and 146, have a width 177 which can be equal to a width of a web of fibrous material which the receiving component may contain. The width 177 can be generally parallel to the lateral axis 162. In some embodiments, the sweep regions 140, 142, 144, and 146, can have the length 175 which is equal to a contact length 250 (shown in FIG. 2B) between calendering rolls. In some embodiments, the sweep regions 140, 142, 144, and 146, can have the length 175 which is less than the contact length 250 (shown in FIG. 2B). In some embodiments, the length 175 can range from about 0.1 mm to about 1.2 mm or any individual number within the range. The length 175 can be generally parallel to the longitudinal axis 160.

Each of the sweep regions 140, 142, 144, and 146, contains the length 175 which is equal to the length 175 of adjacent sweep regions. Additionally, as shown, in some embodiments, the sweep region 140 may share the first boundary 132 with the bond zone 130. Also, in some embodiments, the sweep region 146 can share the second boundary 134 with the bond zone 130.

Each sweep region 140, 142, 144, and 146, contains a bonded area which is defined by the bonding pattern. The percentage of the bonded area in a sweep region is a measure of the fiber-to-fiber bonds within the sweep region. Specifically, the percentage of the bonded area is determined by calculating the area of the fiber-to-fiber bonds within a particular sweep region, and dividing this area by the total area in the sweep region and multiplying by 100.

The bonded areas of the sweep regions 140, 142, 144, and 146, can vary. The variability of the amount of the bonded areas among the sweep regions 140, 142, 144, and 146, can be determined by comparing a value of the largest bonded area of a sweep region to a value of the lowest bonded area of another sweep region. A ratio of the largest bonded area and the lowest bonded area between any two sweep regions is termed the bond ratio. In some embodiments, the bond ratio is greater than or equal to about 1 and less than about 20 or any individual number within the range. In other embodiments, the bond ratio is greater than or equal to about 1 and less than or equal to about 10. In other embodiments, the bond ratio is greater than or equal to about 1 and less than or equal to about 3. In some embodiments, where the bond ratio is 1, there may not be a value of the largest bonded area or a value of the lowest bonded area. In this instance, the value of one bonded area can be divided by the value of another bonded area.

Adding the bonded areas of each of the individual sweep regions can provide the cumulative bonded area. Adding the total areas of each of the individual sweep regions can provide the cumulative total area. Dividing the cumulative bonded area by the cumulative total area can provide the overall bonded area of the bond zone 130, in some embodiments, or the overall bonded area of the nonwoven web 103 in other embodiments.

The bonded area can be formed by any suitable process. Examples of processes for forming the bonded area include a calendaring process (e.g., an embossing process). In one embodiment, the embossing process can be conducted using a general embossing roll. That is, at least one of a pair of rolls is an engraved roll having protrusions which match up with an embossing pattern, and thermal fusion can be conducted by passing the nonwoven web between the rolls. The degree of the thermal fusion can be controlled by adjusting a temperature, contact pressure, etc., of the rolls depending required properties of the nonwoven web being fabricated. The bonded area formation using a calendaring system is described in detail below.

Figure 2B:
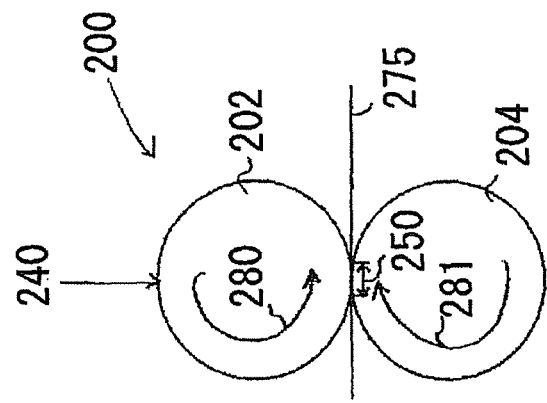
FIG. 2B is an elevation view showing a side of a pair of calendering rolls of the process of FIG. 2A.
Figure 2A:
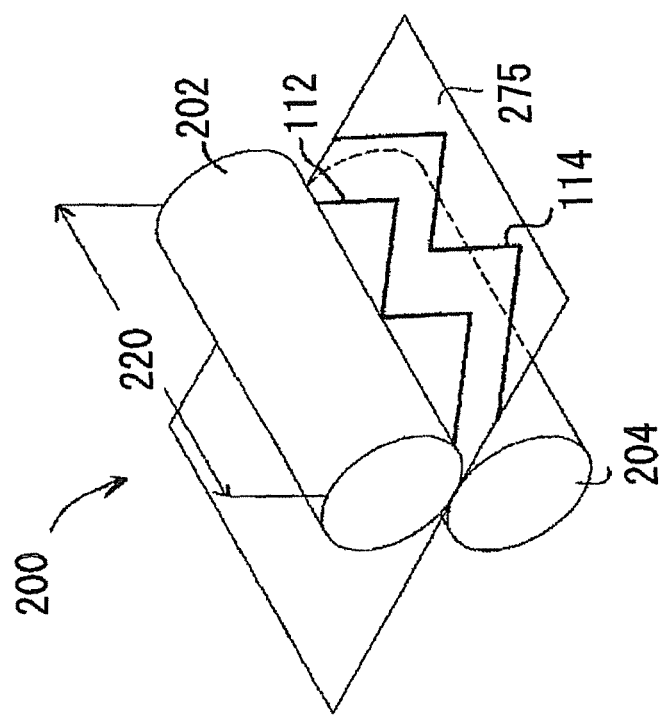
FIG. 2A is a schematic view showing a process for producing bonding patterns in accordance with the subject invention.

As shown in FIGS. 2A and 2B, the bond lines, e.g., 110 (shown in FIG. 1B), 112 and 114, of a receiving component 100 (shown in FIG. 1), in some embodiments, can be produced via a calendering system 200. The calendering system 200 may contain a pair of calendering rolls 202 and 204 which create a nip therebetween. The outer surface of the calender roll 202 and/or the calender roll 204 may contain protrusions (not shown) extending outward from their outer surface. These protrusions typically create fiber-to-fiber bonds in a web of fibrous material 275 as the web of fibrous material 275 passes through the nip. The receiving component 100 (shown in FIGS. 1A and 1B) may contain a portion of the web of fibrous material 275.

The web of fibrous material 275 can pass through the calendering rolls 202 and 204 in a direction generally parallel to the longitudinal axis 160 (shown in FIG. 1B) of the receiving component 100 (shown in FIGS. 1A and 1B). Specifically, the longitudinal axis 160 (shown in FIG. 1B) of the receiving component 100 (shown in FIGS. 1A and 1B) can be generally parallel to a machine direction of the calendering system 200. The calendering rolls 202 and 204 can rotate in direction shown by arrows 280 and 281 (shown in FIG. 2B), respectively.

In some embodiments, the calendering rolls 202 and/or 204 can be heated. The calendering rolls 202 and 204 can provide energy to the web of fibrous material 275 as the web of fibrous material 275 passes through the nip. Additionally, in some embodiments, a force 240 can be applied to the calendering rolls 202 and/or 204 such that a pressure is applied to the web of fibrous material 275 as it passes through the nip. The force 240 which can be applied to the calendering rolls 202 and/or 204 is discussed hereafter.

The surface to surface contact of the calendering rolls 202 and 204 can define the contact length 250. The contact length 250 is defined by a portion of the calender roll 202 and a portion of the calender roll 204 which are in contact with the web of fibrous material 275 (shown in FIG. 2A) as the web of fibrous material 275 (shown in FIG. 2A) passes through the nip. In some embodiments, the contact length 250 can be determined via the Hertzian equation below. The Hertzian equation assumes that the calendering rolls 202 and 204 are made from homogeneous, isotropic material, and further assumes the validity of Hooke's law. Other assumptions include that the calendering rolls 202 and 204 have equal diameters; that the calendering rolls 202 and 204 are created from material which has the same elastic modulus; and that the width 220 of the calendering rolls 202 and 204 are at least as wide as the width 177 (shown in FIG. 1B) of the sweep regions. The contact length 250 can be found via the following equation:

$$X = \sqrt{\frac{8FR(1-v^2)}{\pi EL}}$$

where X is ½ the width of the contact area;
R is the radius of the calender roll 202 or 204 in millimeters;
F is the force applied in Newtons/mm;
E is the elastic modulus of the material of the calender rolls 202 and 204;
L is the width of the calender rolls 202 and 204 (as shown 220); and
v is Poisson's ratio.

Where the calendering rolls do not have equal diameters, one skilled in the art could rederive the above equation taking into account the unequal diameters of the calendering rolls. Where the calendering rolls are not made from materials which have equal elastic moduli, one skilled in the art could rederive the above equation taking into account the unequal elastic moduli of the calendering rolls.

In some embodiments, where the calendering rolls are made of steel, the elastic modulus E can be equal to about 210,000 N/mm$^2$, Poisson's ratio can be about 0.3, and applied force F can be between about 30 N/mm to about 150 N/mm. As mentioned above, X is equal to about ½ of the contact length 250. Thus, multiplying X by two provides the contact length 250. In some embodiments, the contact area can be in a range from about 0.1 mm to about 1.2 mm or any individual number within the range. In some embodiments, the contact area can be in a range from about 0.7 mm to about 1.0 mm.

One advantage of the subject invention is that because of the ratio of larger bonded area to lesser bonded of the subject invention, pressure fluctuations during the calendering process can be reduced. For example, in conventional receiving components where bond areas vary among sweep regions by more than 2000%, the contact area of the calendering rolls producing these bonded areas varies by more than 2000% also. Consequently, if the force applied to the calender rolls is constant, the pressure applied to a web of fibrous material as it passes through the nip of the calender rolls varies by more than 2000% as well. In conventional receiving components pressure fluctuations of greater than 2000% can occur when some sweep regions contain a 0% bonded area, thereby yielding a ratio of larger bonded area to lesser bonded area which is infinite. The zero percent bonded area can occur, for example, when a first bond line and a second bond line are separated by a finite distance in a direction generally parallel to the longitudinal axis of the receiving component which is equal to at least the length of a sweep region. As another example, pressure fluctuations of greater than 2000% can also occur where there is too much overlap between bond lines or too little. The overlap between bond lines is discussed further with regard to FIGS. 3A, 3B, and 3C.

From a process perspective, the pressure fluctuations of greater than 2000% can cause process instabilities. For example, the extreme pressure fluctuations can cause premature failure of the protrusions on the calender rolls.

From a product/material performance perspective pressure fluctuations of greater than 2000% are also not typically desirable. For example, a sweep region having 0% bonded area can provide low shear capability and potentially poor refastenability results. Specifically, because less loose fiber ends are bonded within this sweep region, fuzzing can result during multiple opening and closing cycles with suitable engaging components.

Also, sweep regions having 0% bonded area can reduce the strength in a direction parallel to a lateral axis of the receiving component. The lateral axis of the receiving component, in some embodiments can be associated with the direction of shear in many instances. For example, in a fastened state, the lateral axis of the receiving component can be generally parallel to the direction of shear. For example, referring to FIG. 8A momentarily, in a fastened state, shear forces can act along a primary direction of shear 775 which is generally parallel to a lateral axis of a receiving component 740. Where there is no overlap between adjacent bond lines, the receiving component material in between adjacent bond lines remains free to move with the applied shear force.

In contrast, where the overlap between bond lines causes pressure fluctuations of greater than 2000%, the concentration of fiber-to-fiber bond sites in the region of overlap will generally provide poor fastenability results. For example, as stated previously, engaging components generally are not able to engage receiving components at the bonded areas.

Additionally, the pressure fluctuations of greater than 2000% can also cause variable bonding quality, as discussed previously. When pressure fluctuations are greater than 2000%, fiber-to-fiber bonds in the lesser bonded area sweep regions experience higher pressure than larger bonded area sweep regions and can incur holes because of the higher pressure. Also, the fiber-to-fiber-bonds in the larger bonded area sweep regions can experience lower pressure than lesser bonded area sweep regions and can incur less fiber-to-fiber bonds because of the lower pressure. Specifically, the lower pressure, in some cases, can merely compress fibers instead of actually bonding them.

Figure 2C:
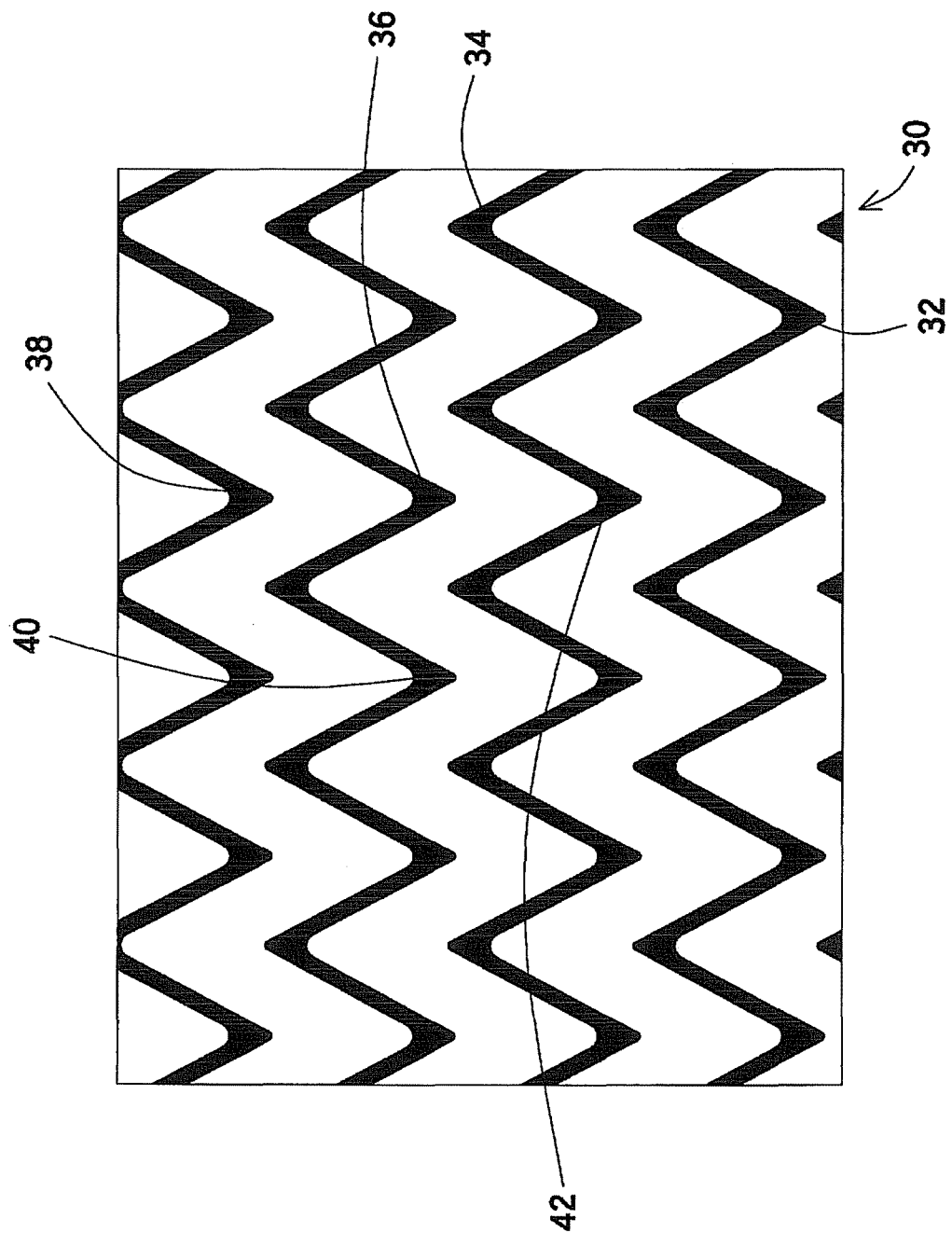
FIG. 2C is a plan view showing a receiving component containing a nonwoven web in accordance with the subject invention.

As shown in FIG. 2C, a receiving component 30 was constructed in accordance with the subject invention and incurred some defects at some locations, e.g., 32, 34, 36, 38, 40, and 42. However, when the bond ratio of the receiving component 30 is about 20 or less, for example, about 1.8, the number of the defects is within an allowable range. In contract, when the bond ratio is above 20 or more, an unacceptable amount of defects may occur in a receiving component.

In contrast with conventional receiving components, a receiving component containing the nonwoven web in accordance with the subject invention reduces pressure fluctuations below about 2000%. The reduction in pressure fluctuation, in part, is accomplished by assuring that a bond area of the receiving component contains a plurality of sweep regions which each have some finite amount of bonded area. Additionally, the sweep regions for receiving components containing the nonwoven web in accordance with the subject invention contain bonded area percentages which reduce pressure fluctuations below about 2000%.

There are several factors which can impact the ratio of larger bonded area to lesser bonded area. Some factors include the overlap of the bond lines, in some embodiments, the orientation angle of the bond lines, the period of the bond lines, and in some embodiments, the orientation of the bond lines during processing. The orientation of the bond lines during processing is discussed further in regard to FIG. 6.

Figure 3A:
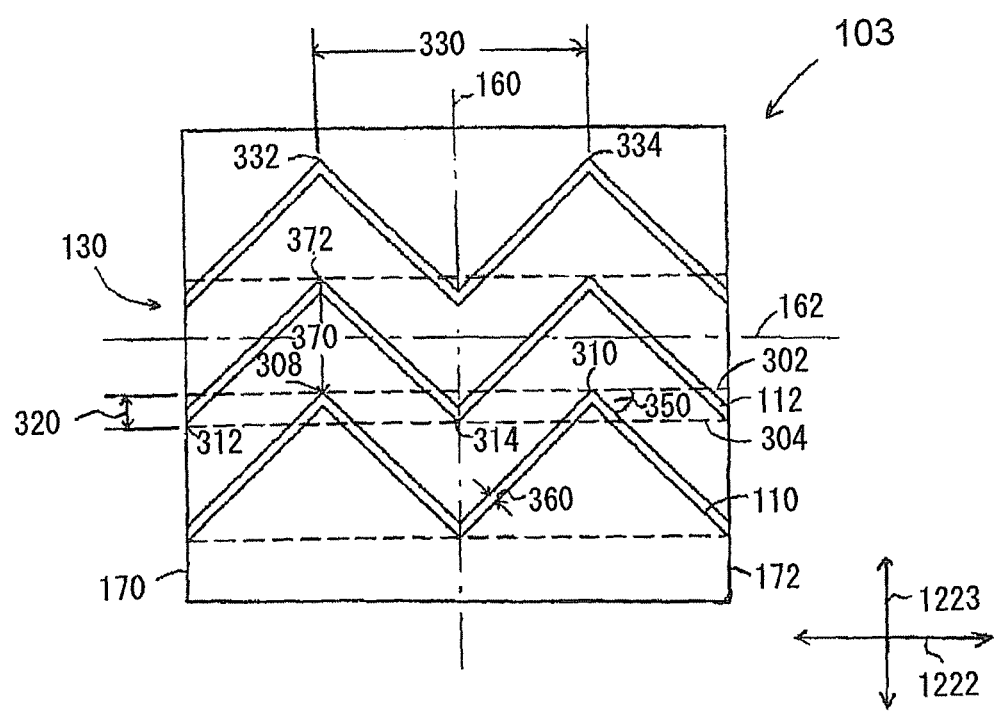
FIGS. 3A-3C are plan views showing the nonwoven web of FIG. 1 highlighting additional features of the bonding pattern.

As shown in FIG. 3A, the overlap 320 is a distance between a first reference line 302 and a second reference line 304. In some embodiments, the overlap 320 is generally parallel to the longitudinal axis 160 and generally parallel to a second direction 1223. The first reference line 302, in some embodiments, can be drawn between two inwardmost points 308 and 310 on the first bond line 110 and can be generally parallel to the lateral axis 162. In some embodiments, the second reference line 304 can be drawn between two inwardmost points 312 and 314 of the second bond line 112 and can be generally parallel to the lateral axis 162. In some embodiments, the inward most points 308 and 310 of the first bond line 110 can be the points nearest the second bond line 112. Similarly, in some embodiments, the inwardmost point 312 and 314 of the second bond line 112 can be the point nearest the first bond line 110. Where the first bond line 110 does not intersect the second reference line 304, and where the second bond line 112 does not intersect the first reference line 302, there is no overlap between the first bond line 110 and the second bond line 112.

Additionally, FIG. 3A shows a period 330, an orientation angle 350, bond line spacing 370, and a bond line thickness 360. In some embodiments, the period 330 can be the smallest interval after which a periodic function takes the same values. As shown, in some embodiments, the period 330 can be a distance from a first peak 332 of the third bond line 114 to a second peak 334 of the third bond line 114. In embodiments where the first bond line 110 and the second bond line 112 are similar to the third bond line 114, the period 330 can be found similarly for the first bond line 110 and the second bond line 112. An orientation angle 350, where a portion of the first bond line 110 intersects the first reference line 302, is also shown.

The bond line spacing 370 is the distance between the first and second bond lines 110 and 112. For example, in some embodiments, the bond line spacing 370 can be measured from the inwardmost point 308 of the first bond line 110 to the outward most point 372 on the second bond line 112. The outward most point 372 on the second bond line 112, in some embodiments, can be the point nearest the third bond line 114. In some embodiments, the bond line spacing 370 can be generally parallel to the longitudinal axis 160. Any suitable spacing can be used. For example, the spacing 370 between the bond lines can be in a range from about 1 mm to about 20 mm or any individual number within the range. As yet another example, the spacing 370 can be between about 3 mm and about 18 mm. As yet another example, the spacing 370 can be between about 6 mm and about 12 mm.

Similarly, any suitable bond line thickness 360 can be utilized. For example, in some embodiments, the bond line thickness 360 can be in a range from about 0.2 mm to about 5 mm or any individual number within the range. In some embodiments, the bond line thickness 360 can be in a range from about 0.5 mm to about 2 mm. In some embodiments, the bond line thickness 360 can be in a range from about 1 mm to about 1.5 mm.

Any suitable period 330 can be used in conjunction with the subject invention. For example, in some embodiments, the period 330 can be in a range from about 1 mm to about 20 mm or any individual number within the range. In some embodiments, the period 330 can be in a range from about 1.5 mm to about 15 mm. In some embodiments, the period 330 can be in a range from about 5 mm to about 12 mm.

The effect that the overlap of the bond lines has on the ratio of larger bonded area to lesser bonded area is illustrated in Table 1. Table 1 contains prophetic examples, and all calculations contained in Table 1 are based on a zigzag bond line pattern similar to the bond line pattern shown in FIG. 1.

TABLE 1

| | Example# | | | | |
| --- | --- | --- | --- | --- | --- |
| | 1 | 2 | 3 | 4 | 5 |
| Line Thickness (mm) | 1 | 0.5 | 0.5 | 1 | 0.5 |
| orientation angle (degrees) | 63.4 | 63.4 | 63.4 | 63.4 | 63.4 |
| Period "T" (mm) | 9.3 | 9.3 | 9.3 | 9.3 | 9.3 |
| line spacing (mm) | 6 | 6 | 12 | 3 | 3 |
| Contact width (mm) | 0.25 | 0.25 | 0.25 | 0.25 | 0.25 |
| Overlap (mm) | 5.52 | 4.4 | 0 | 8.52 | 7.4 |
| Overall Area, % Bonded | 37.2 | 18.6 | 9.3 | 74.4 | 37.2 |
| Larger Area (mm^2) | 1.12 | 0.56 | 0.28 | 1.75 | 0.91 |
| Lesser Area (mm^2) | 0.56 | 0.28 | 0.00 | 1.68 | 0.84 |
| Larger/Lesser Ratio | 2.00 | 2.00 | infinite | 1.04 | 1.09 |
| Max Area, % Bonded | 48.10 | 24.05 | 12.03 | 75.23 | 39.15 |
| Min Area, % Bonded | 24.06 | 12.03 | 0.00 | 72.16 | 36.08 |
| Max/Min Ratio (%/%) | 2.00 | 2.00 | infinite | 1.04 | 1.09 |

As shown in Table 1 and as discussed previously (see Example 3A), where the overlap of the bond lines is equal to zero, the ratio of larger bonded area to lesser bonded area can be infinite in some instances. In contrast, in the embodiments of the subject invention, the first bond line 110 (shown in FIG. 1) and the second bond line 112 (shown in FIG. 1) overlap one another by a finite amount. As shown, see Examples 1 and 4, as the overlap increases, the ratio of larger area to lesser area decreases.

The overlap can be impacted by the thickness of the bond lines. For example, in Table 1, as the thicknesses of the bond lines decrease, the overlap between the bond lines can similarly decrease (see Examples 1 and 2). Additionally, the thickness of all the bond lines in one pattern can be changed as desired to adjust the overall percent bonded area of the bond pattern. Similarly, the overlap can be impacted by the spacing of the bond lines. For example, in Table 1, as the spacing between the bond lines increase, the overlap between the bond lines decreases (see Examples 1 and 4; 2 and 5).

The effect that the orientation angle 350 has on the ratio of larger bonded area to lesser bonded area is illustrated in Table 2. Table 2 contains prophetic examples, and all calculations contained in Table 2 are based on a zigzag bond line pattern similar to the bond line pattern shown in FIG. 1.

TABLE 2

| | EXAMPLE #: | | | | | |
|---|---|---|---|---|---|---|
| | 6 | 7 | 8 | 9 | 10 | 11 |
| Line Thickness (mm) | 1 | 1 | 1 | 1 | 1 | 1 |
| Orientation Angle (degrees) | 75 | 65 | 60 | 55 | 45 | 65.082 |
| Period (mm) | 9.3 | 9.3 | 9.3 | 9.3 | 9.3 | 9.3 |
| Line Spacing (mm) | 18.7 | 9.8 | 7.53 | 5.86 | 3.54 | 10.01 |
| Contact Length (mm) | 0.5 | 0.5 | 0.5 | 0.5 | 0.5 | 0.5 |
| Overlap (mm) | 2.52 | 2.54 | 2.52 | 2.52 | 2.52 | 2.37 |
| Lesser bonded area (%) | 14.51 | 23.73 | 24.83 | 26.25 | 30.41 | 23.71 |
| Larger bonded area (%) | 22.26 | 25.45 | 31.34 | 38.01 | 53.87 | 23.71 |
| Ratio Larger/Lesser | 1.53 | 1.07 | 1.26 | 1.45 | 1.77 | 1.00 |
| Overall Area % Bonded | 20.7 | 24.1 | 25.0 | 29.8 | 30.7 | 23.71 |

For the examples shown above, the orientation angle 350 (shown in FIG. 3A) is changed for a zigzag bond pattern similar to the bond pattern shown in FIG. 1. As shown, the orientation angle 350 (shown in FIG. 3A) was manipulated from about 75 degrees to about 45 degrees, while maintaining an overlap of about 2.5 mm for most examples. In order to ensure an equal amount of overlap for most examples, the line spacing was also varied for each orientation angle 350 (shown in FIG. 3A). In some examples, the period and the bond line thickness were kept constant.

In Example 6, the orientation angle is at 75 degrees, resulting in the lowest overall percentage of the bonded area of 20.7% compared to the other examples in Table 2. Without wishing to be bound by theory, it is believed that as the overlap remains constant at about 2.5 mm, this low percentage of the bond area is the consequence of the line spacing of 18.7 mm, the line thickness of 1 mm, and the period of 9.3 mm.

As shown in Example 7, at an orientation angle of 65 degrees, while maintaining the overlap at 2.5 mm, the total percentage of bonded area can increase to 24.1% at a line spacing of 9.8 mm. The reduction in the orientation angle by about 10 degrees from Example 6 can reduce the ratio of larger bonded area to lesser bonded area from 1.53 to 1.07.

In accordance with the subject invention, the orientation angle 350, in some embodiments, can range from about 45 degrees to about 75 degrees or any individual number within the range. In other embodiments, the orientation angle 350 can range from about 55 degrees to about 65 degrees. In yet other embodiments, the orientation angle 350 can range from about 60 to about 65 degrees.

Example 11, illustrates, in one particular embodiment, how the ratio of larger to lesser bonded area can be made to equal 1.0 for a zigzag bond line pattern similar to that shown in FIG. 1. In some embodiments, the ratio of larger to lesser bonded area can be equal to about 1.0 by adjusting the bond line thickness in the areas where the bond lines do not overlap. Based on the parameters and the relationships of those parameters discussed herein, the modification of at least one of the parameters and/or a relationship between parameters to achieve the ratio of larger bonded area to lesser bonded area of about 1.0 is contemplated.

The effect that the period has on the ratio of larger bonded area to lesser bonded area is illustrated in Table 3. Table 3 contains prophetic examples, and all calculations contained in Table 3 are based on a zigzag bond line pattern similar to the bond line pattern shown in FIG. 1.

TABLE 3

| | Example # | | | | | | | | |
|---|---|---|---|---|---|---|---|---|---|
| | 12 | 13 | 14 | 15 | 16 | 17 | 18 | 19 | 20 |
| Line Thickness (mm) | 1 | 1 | 1 | 1 | 1 | 1 | 1 | 1 | 1 |
| Orientation angle (degrees) | 60 | 60 | 60 | 60 | 60 | 60 | 60 | 60 | 60 |
| Period (mm) | 5 | 6 | 7 | 8 | 9 | 8 | 9 | 10 | 11 |
| Line Spacing (mm) | 6.2 | 6.2 | 6.2 | 6.2 | 6.2 | 7 | 7.9 | 8.7 | 9.6 |
| Contact Length (mm) | 0.5 | 0.5 | 0.5 | 0.5 | 0.5 | 0.5 | 0.5 | 0.5 | 0.5 |
| Amplitude | 3.17 | 3.6 | 4.03 | 4.46 | 4.9 | 4.46 | 4.9 | 5.33 | 5.76 |
| Overlap (mm) | 0.13 | 1.00 | 1.86 | 2.73 | 3.59 | 1.93 | 1.89 | 1.96 | 1.93 |
| Lesser Area Bonded (%) | 6.16 | 19.17 | 30.72 | 28.87 | 25.66 | 27.83 | 24.3 | 22.63 | 20.22 |
| Larger Area Bonded (%) | 46.19 | 38.49 | 32.99 | 39.38 | 46.00 | 28.87 | 25.66 | 23.09 | 20.99 |
| Ratio larger/lesser Area Bonded | 7.50 | 2.01 | 1.07 | 1.36 | 1.79 | 1.04 | 1.06 | 1.02 | 1.04 |
| Overall Area Bonded (%) | 32.3 | 32.3 | 32.3 | 32.3 | 32.3 | 28.6 | 25.3 | 23.0 | 20.8 |

At an equal percentage of the total bonded area, the determined larger bonded area to lesser bonded area ratio is at 1.07 for a period equal to about 7. The overlap for Example 13 can be about 1.9 mm. Based on the data in Table 3, in some embodiments, the period can range from about 5 mm to about 11 mm or any number within the range. In other embodiments, the period can range from about 6 mm to about 8 mm. In yet other embodiments, the period can be about 7 mm.

As shown in Examples 17-20, the bond line spacing can be adjusted such that overall bonded area is impacted. In some embodiments of the subject invention, the overall bonded area can be in a range from about 10% to about 50% or any individual number within the range. In other embodiments, the overall percentage of bonded area can be between about 20% to about 30%. In yet other embodiments, the overall percentage of bonded area can be between about 20% to about 25%. In other embodiments, the overall bonded area can be less than about 40% while the bonded area in any sweep region is less than about 60%. In other embodiments, the overall bonded area can be less than about 30% while the bonded area in any sweep region can be less than about 50%. In yet other embodiments, the overall bonded area can be between about 20% to about 30% while the bonded area in any sweep region is less than about 40%.

As stated previously, the data in Tables 1, 2, and 3, were based on a zigzag bond line patterns similar to the bond line pattern shown in FIG. 1. However, one skilled in the art could calculate the values for the listed parameters in Tables 1, 2, and 3, for any given bond line pattern or variations thereof. For example, for simple geometries, e.g., consisting of angled and connected straight lines, the values shown in Tables 1, 2, and 3, can be calculated using the geometric and trigonometric relationships of the angled and connected straight lines as done for the bond line patterns shown heretofore. For more complex patterns, for example, those shown in FIGS. 4A-4K, or bond line patterns including shapes such as those of FIGS. 5B-5E, the values of Tables 1, 2, and 3, can be obtained by utilizing computerized image analysis.

In computerized image analysis, the bond pattern in question is digitized such that a color contrast can be reliably measured to determine where bonded and unbonded areas are. For example, unbonded areas may be represented as white pixels and bonded areas may be represented as black pixels. The number of pixels representing a bonded area can be counted and compared to number of pixels representing an unbonded area to determine the percentage of bonded area. Similarly, the period, overlap, bond line thickness, orientation angle, and line spacing can also be measured using computerized image analysis.

Additionally, any data or trends discussed in regard to Tables 1, 2, and 3, are pertinent to the bond line patterns analyzed, e.g., zigzag pattern. Consequently, any data and/or trends discussed regarding Tables 1, 2, and 3, may not be valid for other bond line patterns.

Figure 3B:
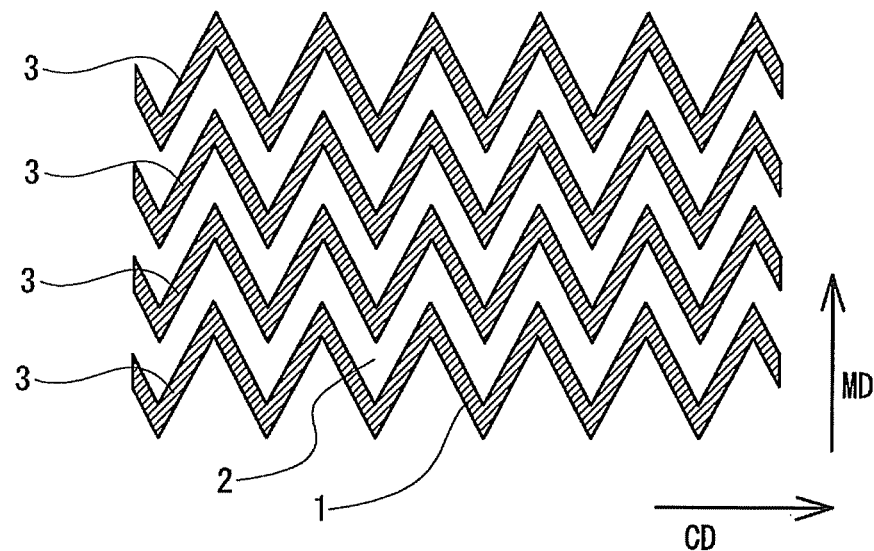
Figure 3C:
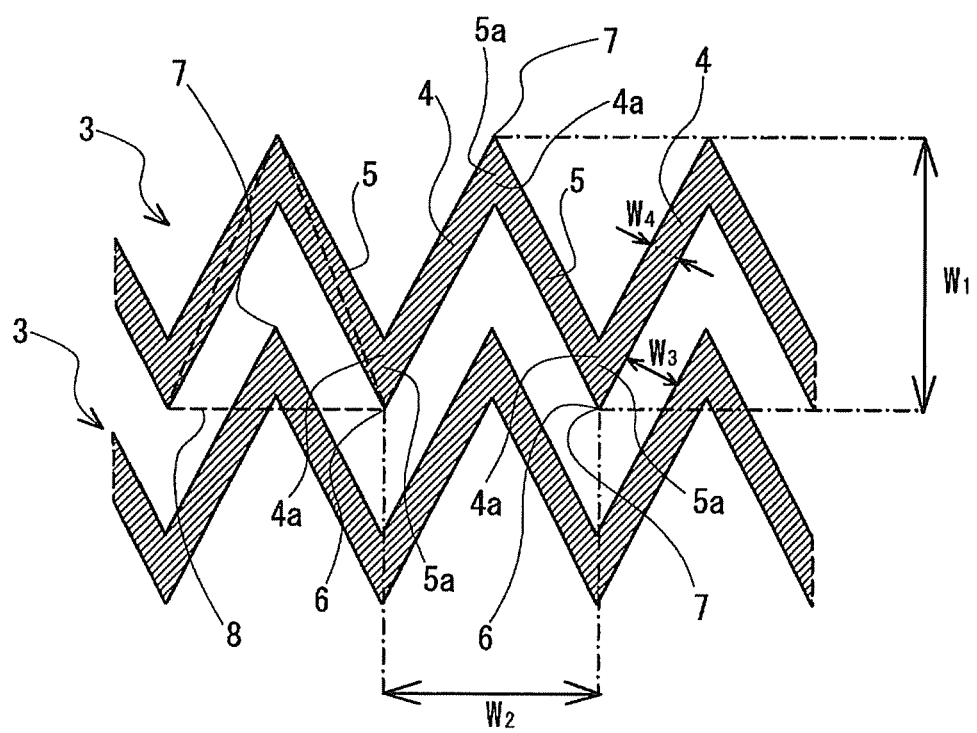

FIGS. 3B and 3C show another exemplary nonwoven web. FIG. 3B illustrates a partial top view of an exemplary nonwoven web for use as a receiving fastener component of the subject invention, and FIG. 3C illustrates an enlarged view of the nonwoven web of FIG. 3B.

In FIG. 3B, embossed portions 1, which is shown by the shaded area, correspond to the area where the crimped composite fiber is thermally compressed and/or fused by an embossing roll. Non-embossed portions 2 are areas between the embossed portions 1 where the crimped composite fiber is not thermally compressed and/or fused and the crimped composite fiber forms loops that undergo an engagement with a hook of an engaging component.

While FIG. 3B illustrates a portion of the nonwoven web for use as a receiving fastener component, the embossed portion 1 is typically formed over the whole area of the nonwoven web for use as a receiving fastener component. Furthermore, the general shape of the nonwoven web for use as a receiving fastener component can be any suitable shape depending on the application and can be any suitable sheet-like shape. For example, a receiving fastener component containing the nonwoven web in accordance with the subject invention and an engaging component containing a hook are previously fixed on two surfaces that are to be connected by, for example, bonding and sewing, respectively, and can be used in a manner that the two surfaces are refastenably connected by hooking the hook of the engaging component on the loop of the receiving component.

Figure 14:
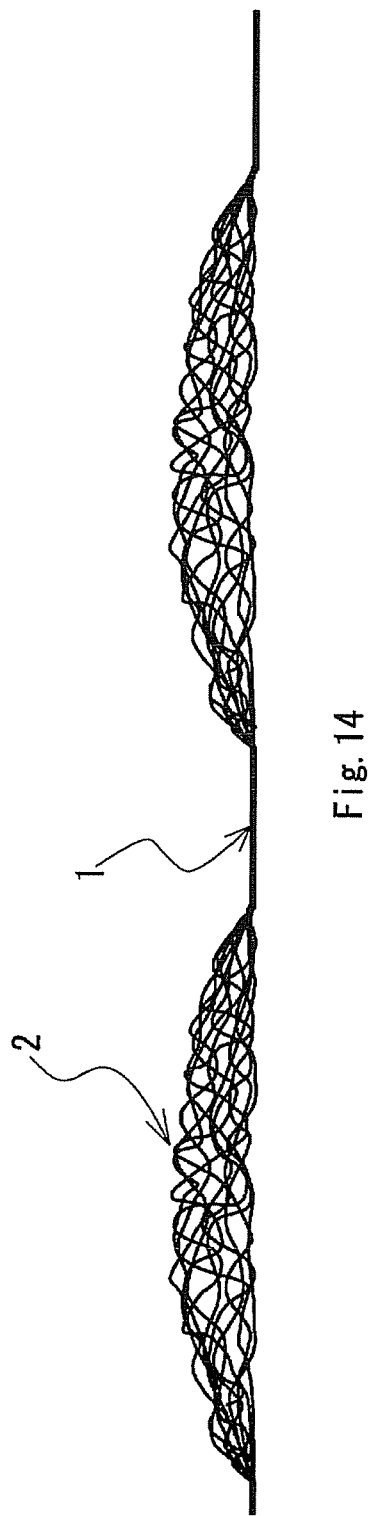
FIG. 14 is a vertical cross sectional view of an exemplary nonwoven web for use as a receiving component of a fastener in accordance with the subject invention.

As shown in FIG. 14, the cross section of the nonwoven web for the receiving fastener component shows recessed embossed portion 1 compared with the non-embossed portion 2. In one embodiment, the difference in height between the non-embossed portion 2 and embossed portion 1 is in the range of about 0.1 to about 2 mm. The shape of the cross section of the projected portion of the engrave of the embossing roll used for forming the embossed portion 1 can be any suitable shape, for example, trapezoid.

As shown in FIG. 3B, the embossed portion 1 of the nonwoven web for the receiving fastener component in this example may contain an embossing pattern containing zigzag unit patterns 3 that are disposed in an MD (Machine Direction) at predetermined intervals, the zigzag unit patterns 3 being continuous in substantially parallel to a CD (Cross Machine Direction) of the embossing roll. Although not shown, the zigzag unit patterns 3 can be disposed in the CD at predetermined intervals, the zigzag unit patterns 3 being continuous in substantially parallel to the MD.

As shown in FIG. 3C, the unit pattern 3 contains zigzag unit patterns containing a plurality of first diagonal lines 4 and a plurality of second diagonal lines 5 that are disposed alternately, the plurality of first diagonal lines 4 being disposed generally parallel with a CD and being inclined to a first side at about the same angle relative to the MD, the second diagonal lines being disposed generally parallel with the CD and being inclined to a second side at about the same angle relative to the MD. The first diagonal lines 4 and second diagonal lines 5 are continuously connected alternately at an end portion 4a of the first diagonal lines 4 and an end portion 5a of the second diagonal lines 5.

Further, as shown in the Figure, a contact point 6 in this example is an outermost point of the contact portion of the first diagonal line 4 and a second diagonal line 5.

Furthermore, an apex 7 is an outermost point of both sides the zigzag of the unit pattern 3, and in this example, the apex is the same point as the contact point 6, which is an outermost point of the contact portion of the first diagonal line 4 and a second diagonal line 5.

As shown in FIG. 3C, in this example, a part of unit pattern 3 can be contained inside a triangle that is formed by adjacent three contact points 6 of the first diagonal line 4 and the second diagonal line 5 (triangle 8 indicated by the dotted lines in FIG. 3C) of the unit pattern 3, the part of unit pattern 3 is adjacent to the triangle in the MD.

In one embodiment, a ratio of $W_1/W_2$ is from about 0.1 to about 10, wherein the width $W_1$ is a width between the apex 7 on one side and the apex 7 on the other side of the unit pattern 3 in the MD and the width $W_2$ is a width between adjacent contact points of the first diagonal line and second diagonal line in the CD. In another embodiment, the ratio of $W_1/W_2$ is from about 0.5 to about 2.0.

When the aforementioned conditions are satisfied, the receiving fastener component has sufficient fastening strength in all of peel strength, repeat peel strength, and tensile shear strength, and at the same time, has high mechanical strength in both of MD and CD.

In particular, it is desirable that the receiving fastener component has sufficient fastening strength in the repeat peel strength and mechanical strength in the CD, and it is believed that with respect to the repeat peel strength and mechanical strength in the CD, overlapping the adjacent unit patterns 3 each other in the MD by including a part of the unit pattern 3 in the inside of the adjacent triangle 8 formed by three adjacent contact points 6 is effective.

In one embodiment, the width $W_1$, which is a width in the MD between an apex 7 on one side and an apex 7 on the other side of the unit pattern 3, is about 3 mm or more and about 50 mm or less. In another embodiment, the width $W_1$, which is a width in the MD between an apex 7 on one side and an apex 7 on the other side of the unit pattern 3, is about 5 mm or more and about 20 mm or less.

In one embodiment, the distance $W_3$, which is a distance between adjacent unit patterns 3, is about 1 mm or more and about 20 mm or less. In another embodiment, the distance $W_3$, which is a distance between adjacent unit patterns 3, is about 2 mm or more and about 8 mm or less.

In one embodiment, the width of line $W_4$ of the unit pattern 3 is in the range of about 0.5 mm or more and about 1.5 mm or less.

In one embodiment, the ratio of the embossed area, which is the value obtained by multiplying 100 by the area ratio of the embossed portion 1 to the sum of the area of embossed portion 1 and the area of non-embossed portion 2, is in the range of about 10% to about 50%. In another embodiment, the ratio of the embossed area is in the range of about 20% to about 30%.

When the aforementioned conditions are satisfied, the nonwoven web has bulkiness as well as high fastening strength and mechanical strength.

Figure 4A:
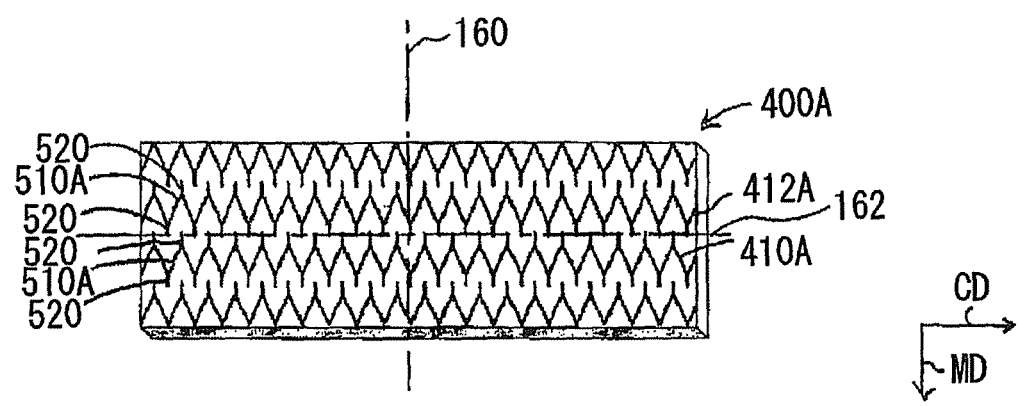
FIGS. 4A-4J are plan views showing other embodiments of a nonwoven web having bond patterns in accordance with the subject invention.

As shown in FIGS. 4A-4K, the overlap between adjacent bond lines can be achieved in a number of different manners. For example, as shown in FIG. 4A, a receiving component 400A constructed in accordance with the subject invention may contain a first bond line 410A and a second bond line 412A. The first bond line 410A and the second bond line 412A may each contain a plurality of repeating units 510A. The repeating units 510A of the first bond line 410A and the second bond line 412A, in some embodiments, can overlap one another via extensions 520 generally extending in a direction parallel to the longitudinal axis 160 from each repeating unit 510A. Also, as shown, in some embodiments, the first and the second bond lines 410A and 412B may contain extensions 520 which extend in a direction generally parallel to the longitudinal axis 160 in between repeating units 510A.

In some embodiments, the extensions 520 may extend at an angle with respect to the longitudinal axis 160. In some embodiments, the extension angle 1350 (shown in FIG. 4K) can be in a range from greater than about 0 degrees to less than about 180 degrees or any individual number within the range. In yet other embodiments, the extension angle 1350 (shown in FIG. 4K) can be in a range of about 30 degrees and less than or equal to about 150 degrees. In yet other embodiments, the extension angle 1350 can be in a range from about 60 degrees to about 120 degrees. In some embodiments, the extension angle 1350 of all bond lines can be similar. In some embodiments, the extension angle 1350 can vary between the bond lines of a bond pattern. Additionally, in some embodiments, the extension angle 1350 can vary among repeating units 510A.

Figure 4B:
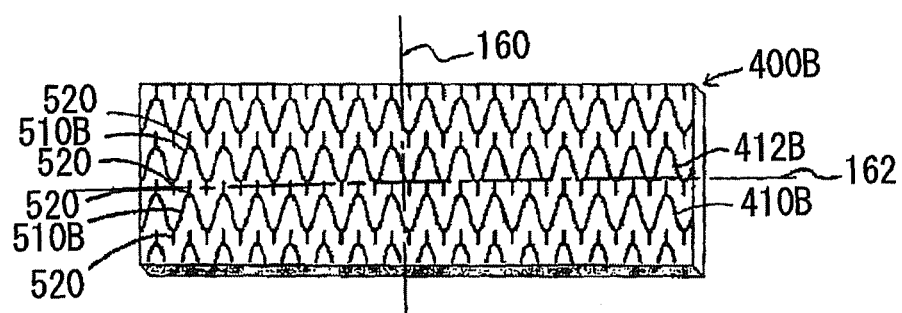

In other embodiments, as shown in FIG. 4B, a receiving component 400B constructed in accordance with the subject invention may contain a first bond line 410B and a second bond line 412B. Similarly, the first bond line 410B and the second bond line 412B may contain a plurality of repeating units 510B having extensions 520. The extensions 520 of the repeating units 510B can be configured similarly to the extensions 520 of the repeating units 510A. Additionally, as shown in FIG. 4B, the bond lines of the subject invention are not limited to rectilinear repeating units 510A. For example, as shown, in some embodiments, the bond lines may contain a plurality of repeating units 510B containing curvilinear segments. As shown, the repeating units 510B appear sinusoidal in nature. Examples of other repeating units are shown in FIGS. 5A-5E.

Figure 4C:
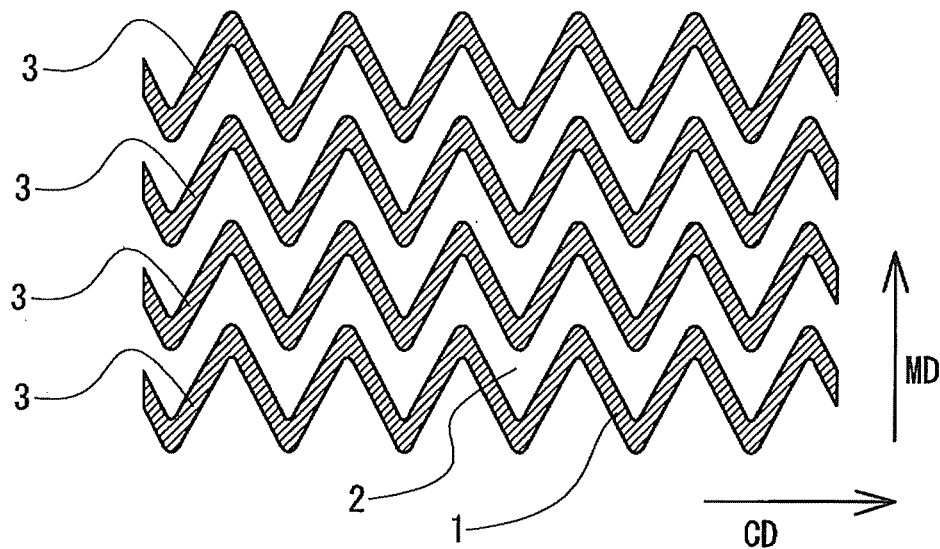
Figure 4D:
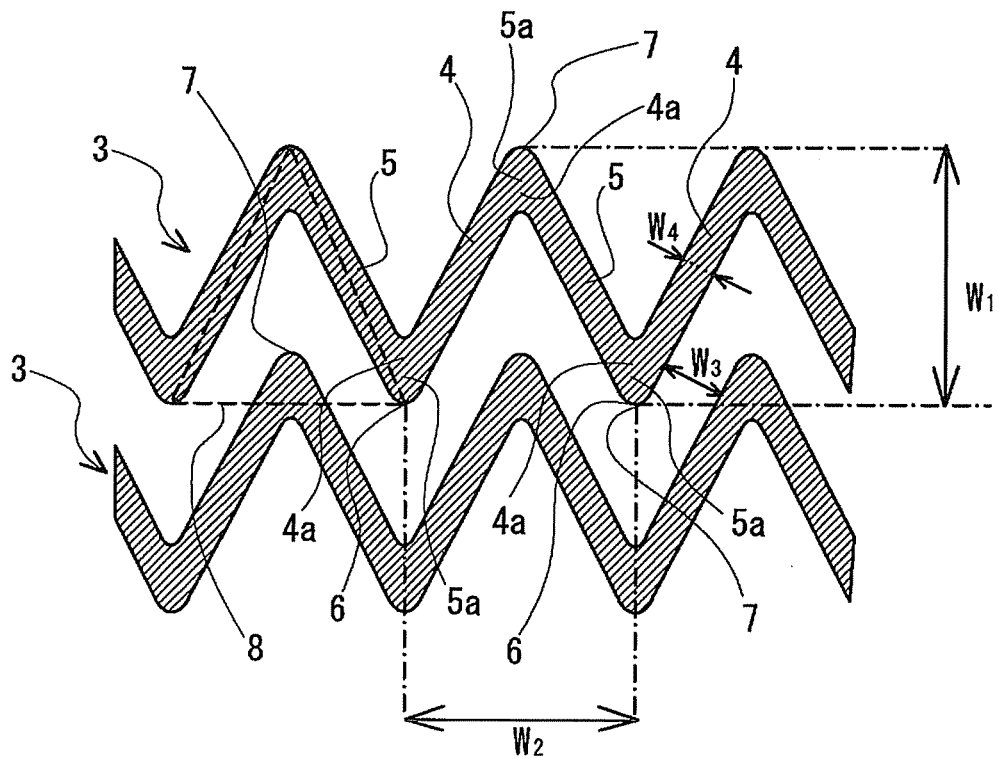

FIG. 4C illustrates another exemplary embodiment of a nonwoven web for use as the receiving fastener component in accordance with the subject invention. FIG. 4D illustrates an enlarged view of a portion of the nonwoven web of FIG. 4C. It is to be appreciated that the components corresponding to FIGS. 3B and 3C are indicated by the same reference numbers in FIGS. 4C and 4D.

The nonwoven web for a receiving fastener component in this example contains essentially the same structure described previously, and, as shown in FIG. 4C, the nonwoven web contains an embossed portion 1 containing zigzag unit patterns 3 that are disposed in an MD at predetermined intervals, the zigzag unit patterns 3 being continuous in substantially parallel to a CD of the embossing roll.

In this example, as shown in FIG. 4D, the unit pattern 3 has a curvature at the apexes 7. In this way, the apexes of the zigzag of the unit pattern 3 in accordance with the subject invention may have a slight roundness.

Figure 4E:
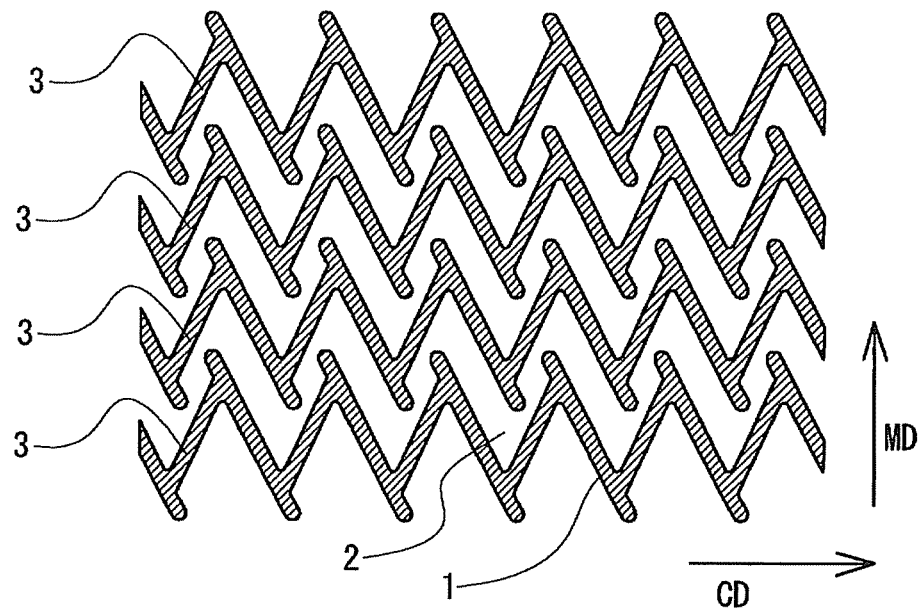
Figure 4F:
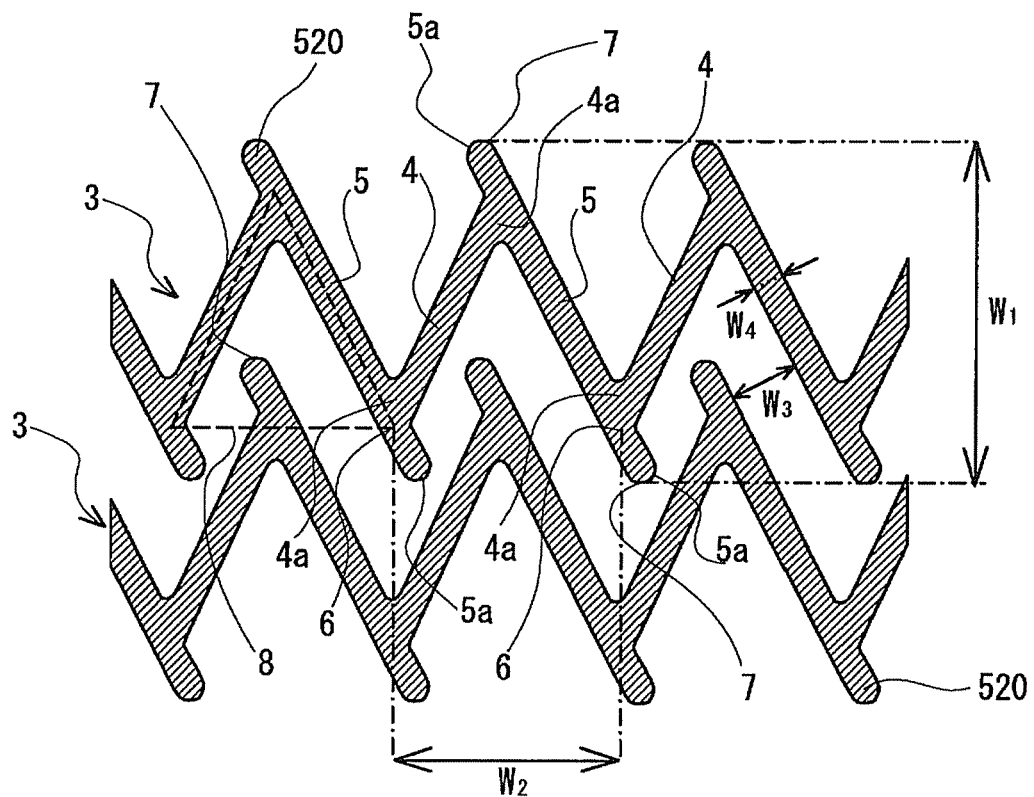

FIG. 4E illustrates a top view of a portion of another exemplary embodiment of a nonwoven web for use as the receiving fastener component in accordance with the subject invention, and FIG. 4F illustrates an enlarged view of a portion of the nonwoven web of FIG. 4E. It is to be appreciated that the components corresponding to FIGS. 3B and 3C are indicated by the same reference numbers in FIGS. 4E and 4F.

The nonwoven web for a receiving fastener component in this example has essentially the same structure as the above-mentioned embodiments, and as shown in FIG. 4E, the nonwoven web contains an embossed portion 1 containing zigzag unit patterns 3 that are disposed in an MD at predetermined intervals, the zigzag unit patterns 3 being continuous generally parallel with a CD of an embossing roll.

The general shape, method for using, shape of the cross section and range of the various numeric values of the nonwoven web for a receiving fastener component can be the same conditions as described in the above embodiments.

As shown in FIG. 4F, the unit pattern 3 contains zigzag unit patterns containing a plurality of first diagonal lines 4 and a plurality of second diagonal lines 5 that are disposed alternately, the plurality of first diagonal lines 4 being disposed generally parallel with a CD and being inclined to a first side at about the same angle relative to the MD, the second diagonal lines being disposed generally parallel with the CD and being inclined to a second side at about the same angle relative to the MD.

In this example, the first diagonal lines 4 and second diagonal lines 5 are continuously connected alternately at an end portion 4a of the first diagonal lines 4 and an end portion 5a of the second diagonal lines 5.

Further, as shown in the FIG. 4F, a contact point 6 in this example is an outermost point of the contact portion of the first diagonal line 4 and a second diagonal line 5 where the outermost point is the near side to an apex 7.

Furthermore, the apex 7 is an outermost point of both sides the unit pattern 3, and in this example, the apex is the end point 5a of the second diagonal line 5.

As shown in FIG. 4F, the adjacent portion to the end point 5a of the second diagonal line 5 slightly projects from the contact point 6. That is, the unit pattern 3 contains extensions 520.

As shown in FIG. 4F, in this example, a part of unit pattern 3 can be contained inside a triangle that is formed by adjacent three contact points 6 of the first diagonal line 4 and the second diagonal line 5 (triangle 8 indicated by the dotted lines in FIG. 4F) of the unit pattern 3, the part of unit pattern 3 is adjacent to the triangle in the MD.

In one embodiment, as described above, a ratio of $W_1/W_2$ is about 0.1 or more and about 10 or less, wherein the width $W_1$ is a width between the apex 7 on one side and the apex 7 on the other side of the unit pattern 3 in the MD and the width $W_2$ is a width between adjacent contact points of the first diagonal line and second diagonal line in the CD. In another embodiment, the ratio of $W_1/W_2$ is about 0.5 or more and about 2.0.

When the aforementioned conditions are satisfied, the receiving fastener component has sufficient fastening strength in all of peel strength, repeat peel strength, and tensile shear strength, and at the same time, has high mechanical strength in both of MD and CD.

Figure 4G:
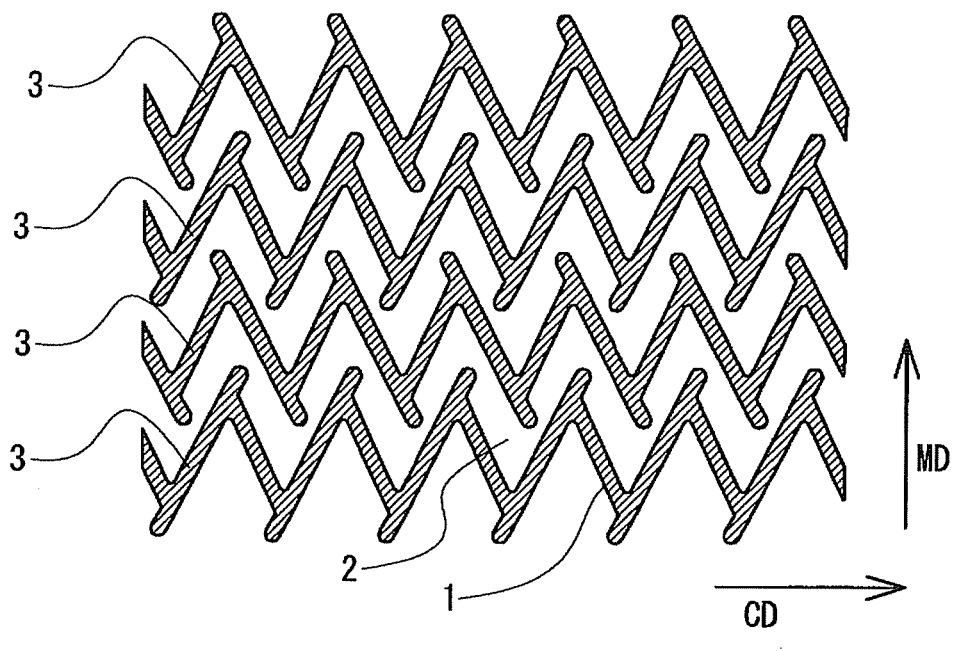
Figure 4H:
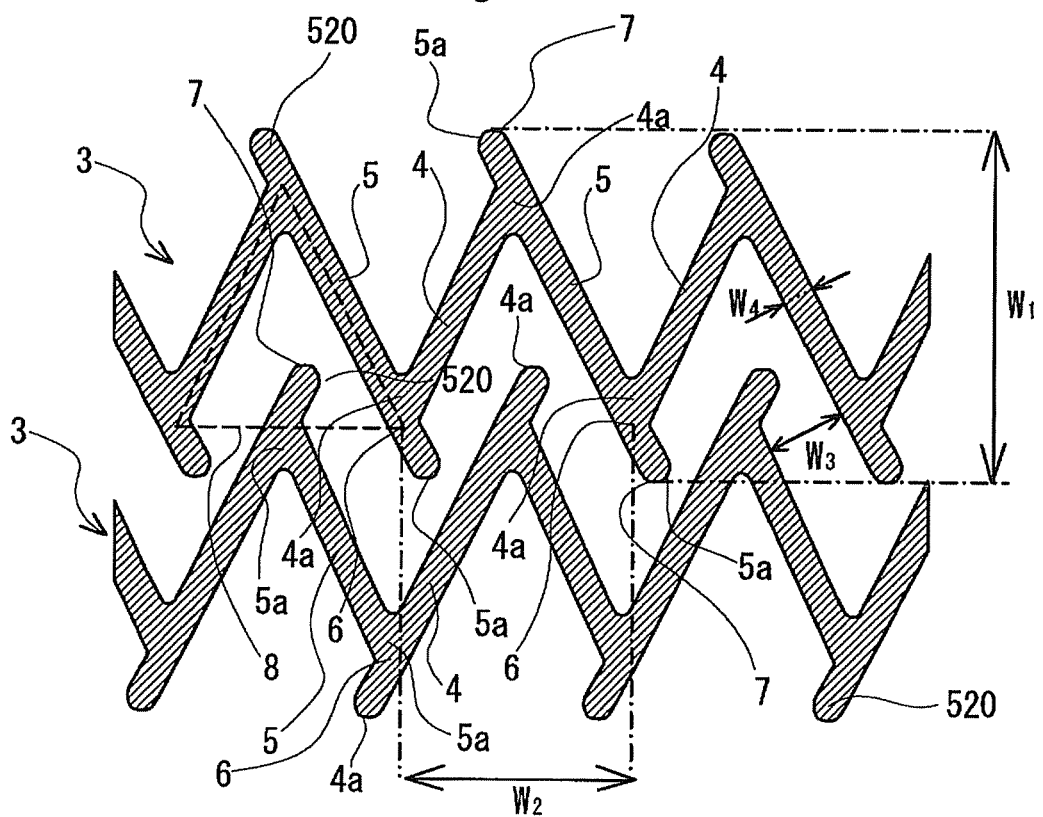

FIG. 4G illustrates a top view of a portion of another exemplary embodiment of a nonwoven web for use as the receiving fastener component in accordance with the subject invention, and FIG. 4H illustrates an enlarged view of a portion of the nonwoven web of FIG. 4G. It is to be appreciated that the components corresponding to FIGS. 4E and 4F are indicated by the same reference numbers in FIGS. 4G and 4H.

The nonwoven web for a receiving fastener component in this example has essentially the same structure as the above-mentioned embodiments, and as shown in FIG. 4G, the nonwoven web contains an embossed portion 1 containing zigzag unit patterns 3 that are disposed in an MD at predetermined intervals, the zigzag unit patterns 3 being continuous generally parallel with a CD of an embossing roll.

In this example, as shown in FIG. 4H, a unit pattern 3 in which an adjacent portion of an end portion 5a of a second diagonal line 5 projects from a contact point 6 and a unit pattern in which an adjacent portion of an end portion 4a of a first diagonal line 4 projects from a contact point 6 are disposed alternately in the MD. The unit pattern 3 contains extensions 520.

That is, one unit pattern 3 is continuous where the first diagonal line 4 and first diagonal line 5 are connected alternately at the end portion 4a of the first diagonal lines 4 and an adjacent portion of the end portion 5a of the second diagonal lines 5.

And, another unit pattern 3 that is adjacent to the above unit pattern 3 is continuous where the first diagonal line 4 and first diagonal line 5 are connected alternately at an adjacent portion of the end portion 4a of the first diagonal lines 4 and the end portion 5a of the second diagonal lines 5.

A part of unit pattern 3 can be contained inside a triangle that is formed by adjacent three contact points 6 of the first diagonal line 4 and the second diagonal line 5 of the unit pattern 3, the part of unit pattern 3 being adjacent to the triangle in the MD. In FIG. 4H, the end portion 5a of the second diagonal line 5 of one unit pattern 3 overlaps a triangle that is formed by adjacent three contact points 6 of adjacent other unit pattern 3, and the end portion 4a of the first diagonal line 4 of the other unit pattern 3 overlaps a triangle that is formed by adjacent three contact points 6 of adjacent one unit pattern 3.

A receiving fastener component containing the nonwoven web in this example has sufficient fastening strength in all of peel strength, repeat peel strength, and tensile shear strength, and at the same time, has high mechanical strength in both of MD and CD.

Figure 4I:
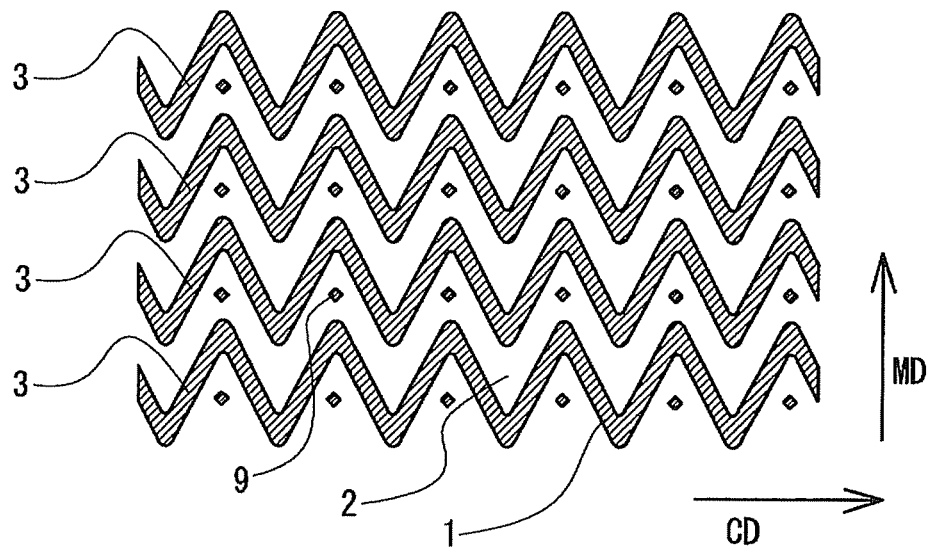
Figure 4J:
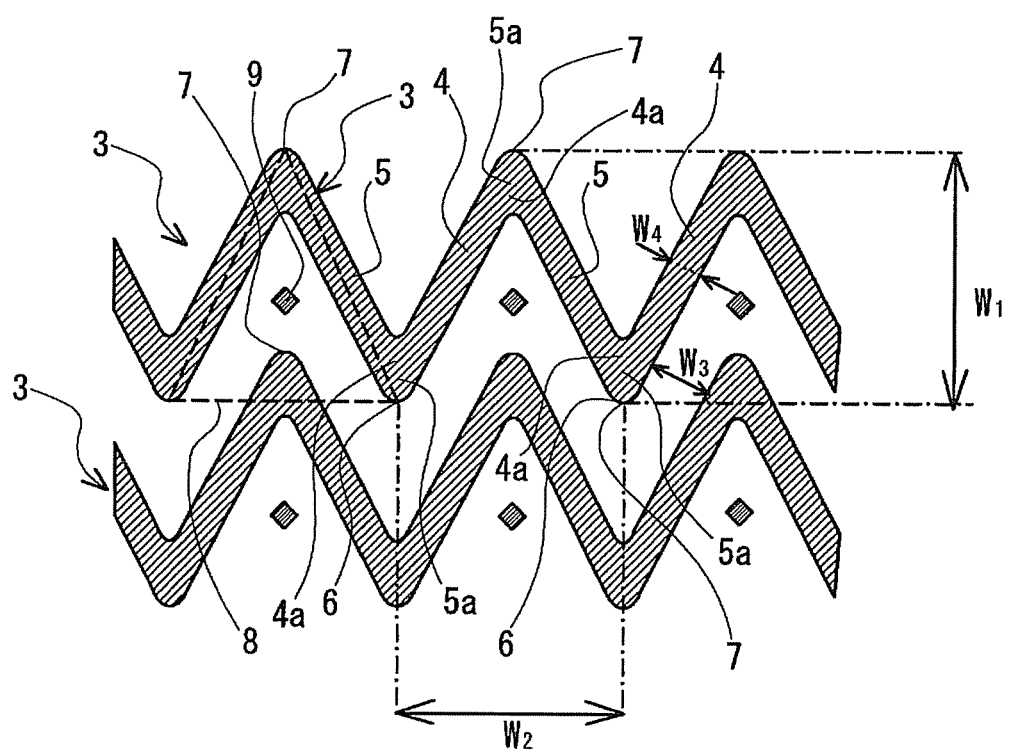
Figure 4K:
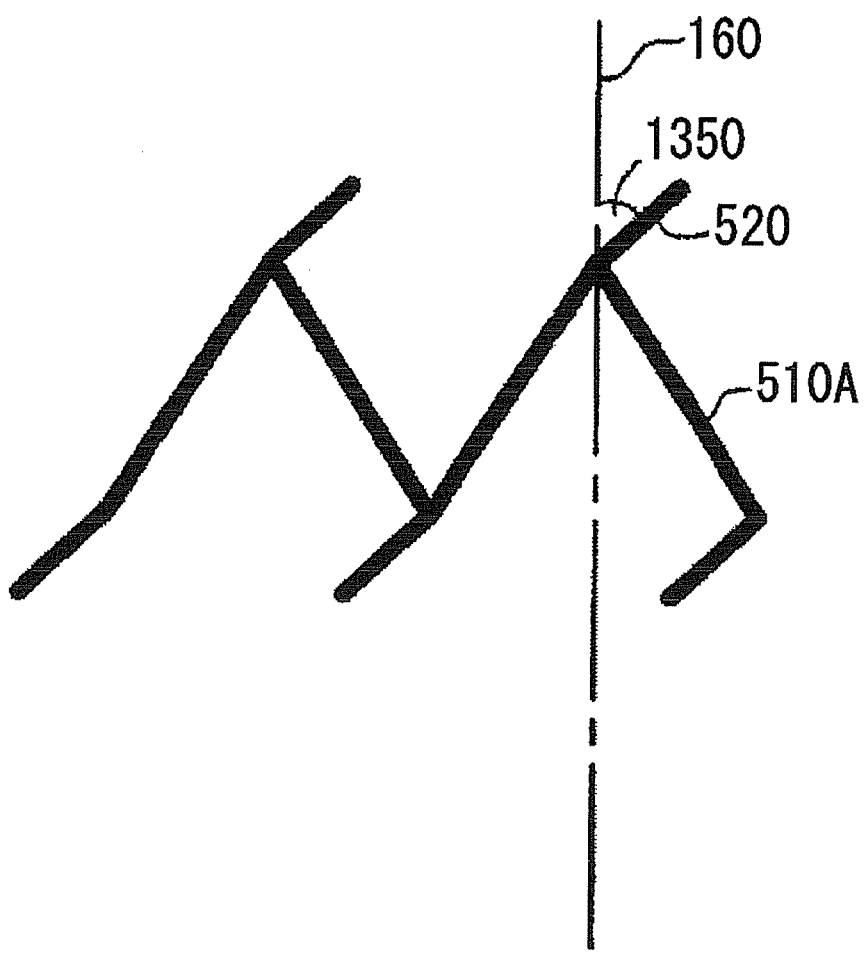
FIG. 4K is a close up view showing a section of the nonwoven web of FIG. 4A.

FIG. 4I illustrates a top view of a portion of another exemplary embodiment of a nonwoven web for use as the receiving fastener component in accordance with the subject invention, and FIG. 4J illustrates an enlarged view of a portion of the nonwoven web of FIG. 4I. It is to be appreciated that the components corresponding to FIGS. 3B and 3C are indicated by the same reference numbers in FIGS. 4I and 4J.

The nonwoven web for a receiving fastener component in this example has essentially the same structure as the above-mentioned embodiments, and as shown in FIG. 4I, the nonwoven web contains an embossed portion 1 containing zigzag unit patterns 3 that are disposed in an MD at predetermined intervals, the zigzag unit patterns 3 being continuous generally parallel with a CD of an embossing roll.

The general shape, method for using, shape of the cross section and range of the various numeric values of the nonwoven web for a receiving fastener component can be the same conditions as described in the above embodiments in connection with FIGS. 3B and 3C.

As shown in FIG. 4J, the unit pattern 3 contains zigzag unit patterns containing a plurality of first diagonal lines 4 and a plurality of second diagonal lines 5 that are disposed alternately, the plurality of first diagonal lines 4 being disposed generally parallel with a CD and being inclined to a first side at about the same angle relative to the MD, the second diagonal lines being disposed generally parallel with the CD and being inclined to a second side at about the same angle relative to the MD. The first diagonal lines 4 and second diagonal lines 5 are continuously connected alternately at an end portion 4a of the first diagonal lines 4 and an end portion 5a of the second diagonal lines 5.

As shown in FIG. 4J, a part of unit pattern 3 can be contained inside a triangle that is formed by adjacent three contact points 6 of the first diagonal line 4 and the second diagonal line 5 (triangle 8 indicated by the dotted lines in FIG. 4J) of the unit pattern 3, the part of unit pattern 3 is adjacent to the triangle in the MD.

In one embodiment, as described above, a ratio of $W_1/W_2$ is about 0.1 or more and about 10 or less, wherein the width $W_1$ is a width between the apex 7 on one side and the apex 7 on the other side of the unit pattern 3 in the MD and the width $W_2$ is a width between adjacent contact points of the first diagonal line and second diagonal line in the CD. In another embodiment, the ratio of $W_1/W_2$ is about 0.5 or more and about 2.0 or less Also, as shown in FIGS. 4I and 4J, the nonwoven web contains a dot pattern 9 that is thermally fused by an embossing roll between adjacent two unit patterns 3. That is, the embossed portion 1 contains the unit pattern 3 and dot pattern 9.

The dot pattern 9 can be disposed at any suitable location between adjacent two unit patterns 3. The shape of dot pattern 9 can be any suitable shape such as dots or dot-like shape, and the size of the dot can be determined by taking fastening strength, bulkiness, and the like into consideration.

A receiving fastener component containing the nonwoven web in this example has sufficient fastening strength in all of peel strength, repeat peel strength, and tensile shear strength, and at the same time, has high mechanical strength in both of MD and CD.

The extensions 520 of FIGS. 4A, 4B, 4E, 4F, 4G, and 4H, in some embodiments, can be straight lines as shown. However, the extensions may contain any suitable shape. For example, in some embodiments, the extensions 520 may contain rectangles, circles, triangles, rhomboid like structures, trapezoidal like structures, any suitable polygonal shape, curvilinear lines, angled lines, squiggly lines, combinations thereof, or the like. In other embodiments, the extensions 520 may contain aesthetic designs such as, for example, a graphic or child graphic. The graphic may be any suitable visual image or images. The graphic may include pictorial symbols and/or images, such as, but not limited to, photographs, drawings, embossments, or any other suitable materials utilized to create pictorial symbols and/or images. The pictorial symbols and/or images may include an image of a child, an anthropomorphic image of an animal or object, images of cartoons including well known cartoon characters, images of well known brand logos or the like, and/or images characters specifically created to be associated with the implement of commerce, symbols, such as, but not limited to arrows, indications or motion or movement, and the like, and combinations thereof. Graphics and child graphics are discussed in U.S. Patent Publication No. 2005/0129743A1, U.S. Patent Publication No. 2005/0125923A1, and U.S. Patent Publication No. 2005/0125877A1, all of which are hereby incorporated by reference in for this regard.

Figure 4L:
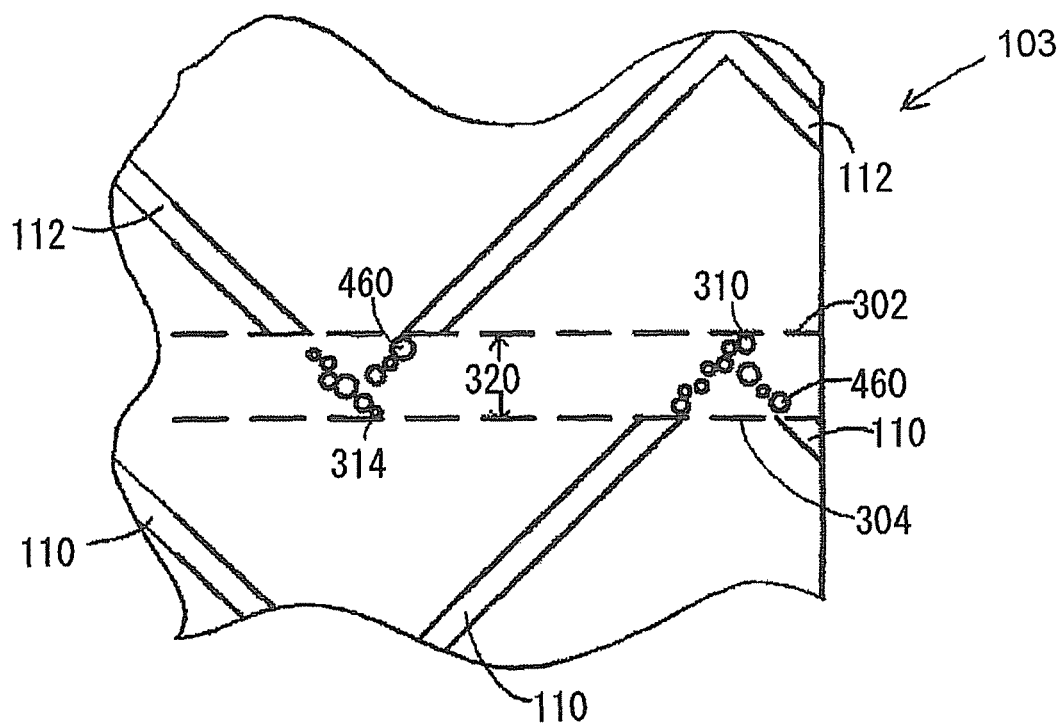
FIG. 4L is a close up view of showing a section of the nonwoven web of FIG. 1.

It has been found that in some embodiments, sweep regions which contain portions of more than one bond line can have higher bonded areas than sweep regions containing a portion of a single bond line. The bonded area of the sweep regions containing portions of more than one bond line can be reduced by any suitable means. For example, as shown in FIG. 4L, the first bond line 110 and/or the second bond line 112 may contain a plurality of bond sites 460 which, in some embodiments, can approximate a line. The plurality of bond sites 460 can be disposed in the overlap 320 of the first bond line 110 and the second bond line 112. In some embodiments, the plurality of bond sites 460 within the overlap 320 can define less bonded area than a continuous bond line in the overlap, thereby reducing the amount of bonded area in the overlap 320. The plurality of bond sites 460 may contain any suitable shape known in the art.

Figure 5A:
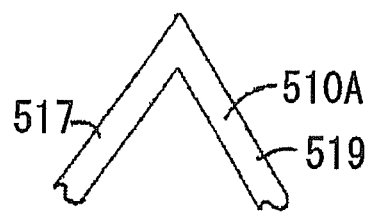
FIGS. 5A-5E are plan views showing repeating units various embodiments for repeating units which can be included in a bond pattern constructed in accordance with the subject invention.
Figure 5B:
Figure 5C:
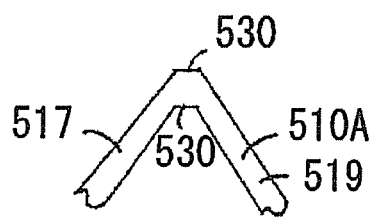

As shown in FIG. 5A, a receiving component constructed in accordance with the subject invention may contain a bond line which includes a plurality of repeating units 510A. The repeating unit 510A, in some embodiments, may contain an open geometrical shape containing rectilinear lines which form a first leg 517 and a second leg 519 of the repeating unit 510A. As shown in FIG. 5B, in some embodiments, the repeating unit 510A may contain rounded edges 529 which join the first leg 517 and the second leg 519 of the repeating unit 510A. The rounded edges 529 can similarly be disposed between adjacent repeating units. As shown in FIG. 5C, the repeating unit 510A may contain flat edges 530 which join the first leg 517 to the second leg 519 of the repeating unit 510A. The flat edges 530 can similarly be disposed between adjacent repeating units.

Figure 5D:
Figure 5E:
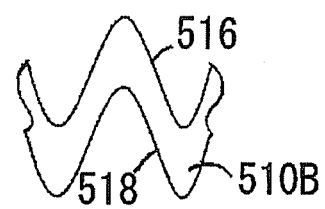

As shown in FIG. 5D, in some embodiments, the repeating unit 510A may contain a plurality of wavy edges 512 and 514 which define the boundary for the first leg 517 and the second leg 519. In embodiments where the bond lines contain a plurality of repeating units having wavy edges, the bond line thickness can be determined by measuring the thickness of the repeating unit 510A in at least about 10 locations and determining the average thickness therefrom. Additionally, as shown in FIG. 5E, in some embodiments, the repeating unit 510B may contain a plurality of sinusoidal shaped edges 516 and 518.

The repeating units 510A and 510B of the subject invention may contain any suitable shape or a combination of shapes. In some embodiments, a bond line of the subject invention may contain different repeating units within the bond line. In other embodiments, the repeating units in a first bond line may be similar while a second bond line contains a repeating unit which is different from the repeating units of the first bond line.

As mentioned previously, the orientation of the bond lines during processing can also impact the ratio of larger bonded area to lesser bonded area. In a receiving component constructed in accordance with the subject invention, a longitudinal axis of the receiving component can be generally parallel to a machine direction during processing. In some embodiments, the resulting bond lines can extend from the first longitudinal edge 170 (shown in FIGS. 1B and 3) to a second longitudinal edge 172 (shown in FIGS. 1B and 3).

Figure 6:
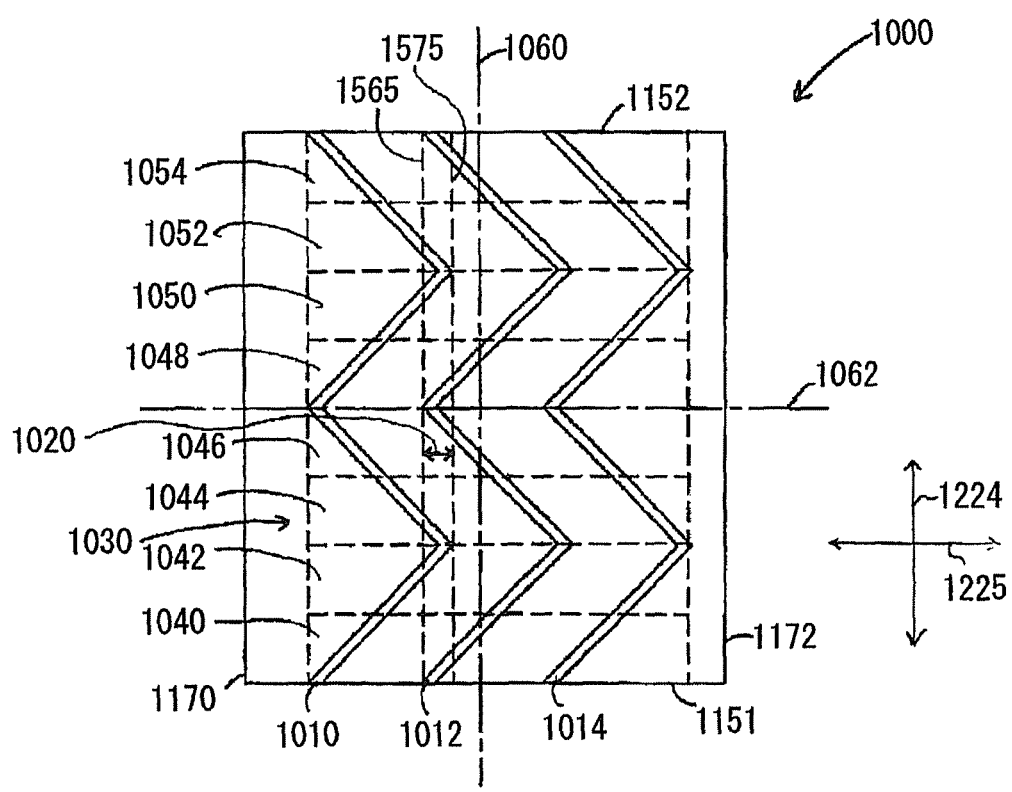
FIG. 6 is a plan view showing another embodiment of a nonwoven web constructed in accordance with the subject invention.

In contrast, as shown in FIG. 6, in some embodiments, a receiving component 1000 constructed in accordance with the subject invention may contain a first bond line 1010, a second bond line 1012, and a third bond line 1014. In some embodiments, each of the first bond line 1010, the second bond line 1012, and the third bond line 1014, can extend from a first end edge 1151 to a second end edge 1152 of the receiving component 1000 in a first direction 1224 which is generally parallel to a longitudinal axis 1060. The receiving component 1000 may contain a bond zone 1030 which circumscribes a bond line nearest a first longitudinal edge 1170 and a bond line nearest a second longitudinal edge 1172 and any bond lines in between. For example, as shown, the bond zone 1030 can circumscribe the first bond lines 1010, the second bond line 1012, and the third bond line 1014. Embodiments are contemplated where the receiving component contains more than three bond lines and fewer than three bond lines.

The bond zone 1030 contains a plurality of sweep regions 1040, 1042, 1044, 1046, 1048, 1050, 1052, and 1054. The plurality of sweep regions 1040, 1042, 1044, 1046, 1048, 1050, 1052, and 1054, may contain similar lengths and widths to the sweep regions discussed heretofore. As shown, in some embodiments, each sweep region of the plurality of sweep regions 1040, 1042, 1044, 1046, 1048, 1050, 1052, and 1054, may contain a portion of the first bond line 1010, a portion of the second bond line 1012, and a portion of the third bond line 1014.

Similar to the bond line pattern shown in FIG. 1B, in the bond line pattern of FIG. 6, each sweep region has some finite amount of bonded area. The first bond line 1010 can overlap the second bond line 1012, and the second bond line 1012 can overlap the third bond line 1014. However, in contrast to the overlap 320 (shown in FIG. 3) of the receiving component 100 (shown in FIGS. 1 and 3) the overlap 1020 of the receiving component 1000 can be generally parallel to the lateral axis 1062. Similarly, the second bond line 1012 can overlap the third bond line 1014.

The overlap 1020 can be the distance between a third reference line 1565 and a fourth reference line 1575. In some embodiments, the overlap 1020 can be generally parallel to a second direction 1225. The third reference line 1565, in some embodiments, can be generally parallel to longitudinal axis 1060. Similarly, the fourth reference line 1575, in some embodiments, can be generally parallel to the longitudinal axis 1060. The third reference line 1565 can extend from the first end edge 1151 to the second end edge 1152 and can intersect the inwardmost points of the first bond line 1010. The inwardmost points of the first bond line 1010 are those points which are nearest the second bond line 1012. The fourth reference line 1575 can extend from the first end edge 1151 to the second end edge 1152 and can intersect the outwardmost points of the second bond line 1012. The outwardmost points of the second bond line 1012, when referencing the overlap 1020 between the first bond line 1010 and the second bond line 1012, are those points on the second bond line 1012 which are nearest the first bond line 1010.

The nonwoven web for a receiving fastener component in accordance with the subject invention is described in detail below. The nonwoven web for a receiving fastener component in accordance with the subject invention contains a nonwoven web containing a crimped composite fiber (hereinafter, the crimped composite fiber may be referred to as a composite fiber) or a nonwoven laminate containing the nonwoven web. The crimped composite fiber contains a first propylene polymer and a second propylene polymer. The first and second propylene polymers are arranged to occupy substantially separate areas at the cross section of the composite fiber and extend continually in a longitudinal direction, and each of the first and second propylene polymers forms at least a portion of the peripheral surface continuously along the longitudinal direction of the composite fiber. It is desirable that the second propylene polymer forms at least about 50% of the peripheral surface. That is, the composite fiber is a side-by-side type composite fiber where the first propylene polymer and the second propylene polymer extend side-by-side in the longitudinal direction of the composite fiber.

Figure 9B:
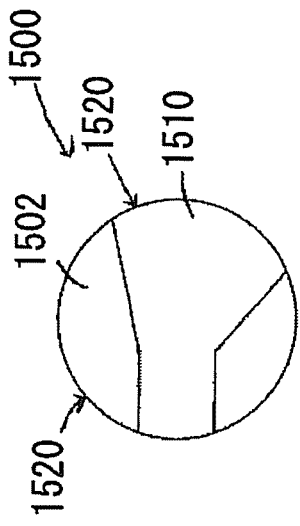
FIGS. 9A-9C illustrate cross section views of exemplary composite fibers in accordance with the subject invention.
Figure 9C:
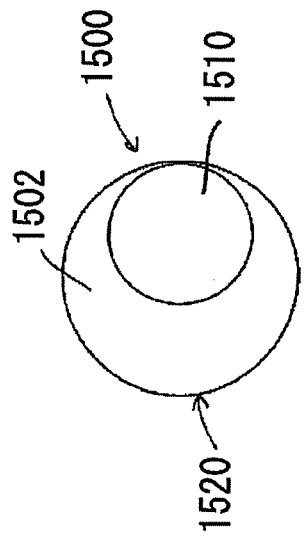
Figure 9A:
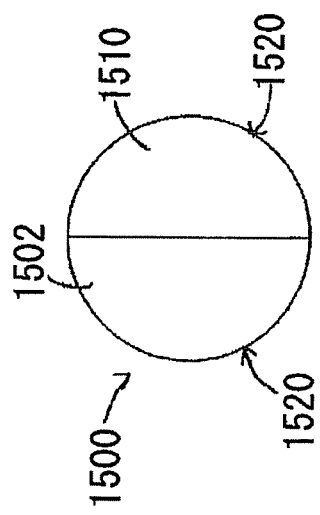

In some embodiments, as shown in FIG. 9A, a composite fiber 1500 can be a side-by-side type composite fiber where a first propylene polymer 1502 and a second propylene polymer 1510 extend side-by-side in the length direction of the composite fiber such that the first and the second propylene polymers 1502 and 1510 each form about 50% of a peripheral surface 1520 of the composite fiber 1500.

The first propylene polymer 1502 and the second propylene polymer 1510 can be arranged in any suitable configuration which would yield a crimp in the resulting fiber 1500. For example, in some embodiments, as shown in FIG. 9B, the second propylene polymer 1510 may form a cross like pattern within the first propylene polymer 1502 which is asymmetrically distributed within the first propylene polymer. In some embodiments, as shown in FIG. 9C, the second propylene polymer 1510 can be completely surrounded by the first propylene polymer 1502 such that the first propylene polymer 1502 contains about 100% of the peripheral surface 1520 of the composite fiber 1500. The second propylene polymer 1510 can be distributed within the first propylene polymer 1502 asymmetrically such that a crimp results in the resulting fiber 1500.

Additionally, embodiments are contemplated where the second propylene polymer 1510 contains any number greater than about 50% of the peripheral surface 1520 of the composite fiber 1500. Additionally, embodiments are contemplated where the second propylene polymer 1510 contains any number less than about 50% of the peripheral surface 1520 of the composite fiber 1500. Also, the first propylene polymer 1502 can be configured similarly to the second propylene polymer 1510 and vice versa. Embodiments are contemplated where fibers are crimped such that they curl or form helical structures.

In one embodiment, a melting point of the first propylene polymer measured by differential scanning calorimetry (DSC) is higher than a melting point of the second propylene polymer by about 15° C. or more. In another embodiment, a melting point of the first propylene polymer measured by differential scanning calorimetry (DSC) is higher than a melting point of the second propylene polymer by about 15° C. or more and about 60° C. or less.

In one embodiment, a weight ratio of the first propylene polymer to the second propylene polymer is from about 50/50 to about 5/95. In another embodiment, a weight ratio of the first propylene polymer to the second propylene polymer is from about 40/60 to about 10/90. In yet another embodiment, a weight ratio of the first propylene polymer to the second propylene polymer is from about 30/70 to about 10/90.

In some embodiments, the melt-flow rate of the first and second propylene polymers measured according to the specification of ASTM D1238 (MFR: measuring temperature 230° C., load 2.16 kg) (second propylene polymer/first propylene polymer) can be in the range of about 0.8 to about 1.2 or any individual number within the range. In some embodiments, the melt-flow rate can be in the range of about 0.9 to about 1.1.

In some embodiments, the area ratio of the first propylene polymer and the second propylene polymer at the cross section of the composite fiber can be about the same as the weight ratio. For example, in some embodiments, a ratio of the cross sectional area of the first propylene polymer to the cross sectional area of the second propylene polymer can be in a range of about 50/50 to about 5/95 or any ratio within the range. In some embodiments, the ratio can be in the range of about 40/60 to about 10/90 or any ratio within the range. In some embodiments, the ratio can be in the range of about 30/70 to about 10/90 or any ratio within the range.

When the aforementioned conditions are satisfied, a crimped state can be achieved in the composite fiber. A suitable number of crimps according to the specification of JIS L1015 can be in the range of about 5 crimps/25 mm to about 50 crimps/25 mm.

In the subject invention, the measurement of the melting point of the first and second propylene polymers based on DSC was conducted by an instrument of the Perkin Elmer Corp. As the sample was set on a measuring plate, the temperature was increased from 30° C. to 200° C. at a temperature increase rate of 10° C./min; the temperature was retained at 200° C. for 10 minutes; the temperature was reduced to 30° C. at a temperature decrease rate of 10° C./min; the temperature was again increased from 30° C. to 200° C. at a temperature increase rate of 10° C./min and the measurement was made on the second run for increasing the temperature.

In one embodiment, it is desirable that the composite fiber has two or more melting point peaks based on DSC, and the area of the lowest melting point peak is equal to or greater than the area of the higher melting point peak. The measurement of the melting point of the composite fiber based on DSC was conducted by the aforementioned device. The sample was set on a measuring plate, the temperature was increased from 30° C. to 200° C. at a temperature increase rate of 10° C./min, and the measurement was made during the first run for increasing the temperature. In the measurement method, the melting point is obtained as the peak on the endothermic curve, and the area of the melting point peak as well as the value of the melting point can be obtained. When two melting point peaks of the composite fiber obtained by the measuring method during the first run overlap each other, the area can be obtained by estimating a peak that does not have effects of another peak according to the shape of the peak with maximum strength, and the area can be compared with the area of the other peak.

Examples of first and second propylene polymers that can be used for the composite fiber of the subject invention include a propylene homopolymer and copolymer of propylene and one or more of α-olefins with about 2 to about 20 carbon atoms, preferably, about 2 to about 8 carbon atoms such as ethylene, 1-butene, 1-pentene, 1-hexene, 1-octene and 4-methyl-1-pentene, having propylene as a primary structural unit. Among those listed above, a propylene homopolymer or propylene-ethylene random copolymer having an ethylene unit content in the range of about 0 to about 10 mol % and MFR in the range of about 20 to about 200 g/10 min is desirable.

In one embodiment, the first propylene polymer is a propylene homopolymer, and the second propylene polymer is a random copolymer of propylene and a small amount of ethylene having an ethylene unit content in the range of about 10 mol % or less, preferably in the range of about 2 to about 10 mol % in terms of production of a nonwoven web having excellent fastening strength and mechanical strength as well as high bulkiness and softness suitable for use as the fastener receiving component. In this case, the ethylene unit content can be obtained according to a standard method using $^{13}$C-NMR spectral analysis.

In one embodiment, the melting point of the first propylene polymer is about 120° C. or more and about 175° C. or less. In another embodiment, the melting point of the second propylene polymer is about 110° C. or more and about 155° C. or less. The propylene polymers can be produced utilizing a high stereospecific polymeric catalyst.

The composite fiber can contain other components, as needed, as long as the object of the subject invention is not impaired. Examples of other components include heat stabilizers, weather resistance agents, a variety of stabilizers, antistatic agents, slip agents, anti-blocking agents, antifog agents, lubricants, dyes, pigments, natural oils, synthetic oils, waxes, etc.

Examples of stabilizers include antioxidants such as 2,6 di-t-butyl-4-methylphenol (BHT), etc; phenolic antioxidants such as tetrakis[methylene-3-(3,5-di-t-butyl-4-hydroxyphenyl) propionate]methane, β-(3,5-di-t-butyl-4-hydroxyphenyl)alkyl ester propionate, 2,2'-oxamidebis[ethyl-3-(3,5-di-t-butyl-4-hydroxyphenyl) propionate, etc; fatty acid metal salts such as zinc stearate, calcium stearate, calcium 1,2-hydroxystearate, etc; polyhydric alcohol fatty acid esters such as glyceryl monostearate, glyceryl distearate, pentaerythritol monostearate, pentaerythritol distearate, pentaerythritol tristearate, etc; and the like. A single stabilizer can be employed or a mixture of two or more stabilizers can be employed.

Examples of lubricants include oleic acid amide, erucic acid amide, stearic acid amide, etc.

In one embodiment, the composite fiber may contain fillers such as silica, diatomaceous earth, alumina, titanium oxide, magnesium oxide, pumice powder, pumice balloon, aluminum hydroxide, magnesium hydroxide, basic magnesium carbonate, dolomite, calcium sulfate, potassium titanate, barium sulfate, calcium sulfite, talc, clay, mica, asbestos, calcium silicate, montmorillonite, bentonite, graphite, aluminum powder, molybdenum sulfide, etc.

The propylene polymer and the optional components mentioned above can be combined using any suitable conventional method.

The nonwoven web containing the aforementioned composite fiber that is provided with an embossed portion having the pattern described herein can have a very high fastening strength and high mechanical strength when used as a receiving fastener component. Furthermore, the nonwoven web can have high bulkiness as well as excellent softness.

Also, the aforementioned composite fiber can have excellent spinnability and excellent fuzzing resistance. Therefore, high productivity can be achieved, and in particular, fuzzing can be controlled at the time of embossing process, and high-speed processing can be achieved.

The nonwoven web can be formed by any suitable method. Examples of formed nonwoven webs include spunbond, spunbond meltblown spunbond (SMS), spunbond meltblown meltblown spunbond (SMMS), carded, meltblown, and the like. In another embodiment, the nonwoven web can be a high elongation carded (HEC) nonwoven or a deep activation polypropylene (DAPP) nonwoven. Any process known in the art may be used to make the nonwovens.

In one embodiment, the nonwoven web contains fibers that are bonded mechanically. For example, the fibers are needle punched or hydro entangled. Examples of suitable bonding processes for producing the nonwoven web include spun bonding, thermally bonding, bonding by various types of chemical bonding such as latex bonding, powder bonding, and the like.

In one embodiment, the nonwoven web containing the crimped composite fiber can be formed by general composite melt spinning method, and a spun-bonded nonwoven web produced by a spun-bonding method with high productivity is desirable.

In one embodiment, a spun-bonded nonwoven web can be formed by melting the first propylene polymer that forms one area of the composite fiber and the second propylene polymer that forms the other area of the composite fiber by a extruder and the like, respectively, extruding each molten material from a nozzle plate having a composite spinning nozzle configured to extrude and form desired fiber structure, and spinning a composite long fiber.

In one embodiment, the long spun fiber is chilled by cooling air, and tensile is applied with blowing air to form a predetermined fiber size. The fiber is collected as is on a collection belt to deposit to a predetermined thickness, and thermally fused by a bonding process such as an embossing process as a bonding treatment, thereby forming a nonwoven web.

The fibers of the nonwoven web may be of any suitable size and shape. The fibers may contain any suitable cross sectional shape, e.g., circular, elliptical (with or without lobe like extensions), or the like. In one embodiment, the fiber size of the nonwoven web is in the range of about 0.5 denier or more and about 5.0 denier or less. In another embodiment, the fiber size of the nonwoven web is in the range of about 1.0 denier or more and about 4.0 denier. In one embodiment, the basis weight of the nonwoven web is in the range of about 20 g/m² or more and about 80 g/m² or less. In another embodiment, the basis weight of the nonwoven web is in the range of about 30 g/m² or more and about 60 g/m² or less.

The nonwoven web for a receiving component of a fastener in accordance with the subject invention can contain a laminate wherein the nonwoven web containing the above-mentioned crimped composite fibers is disposed as an outermost layer of the laminate and at least one layer is laminated on a backside of the nonwoven web. Any suitable layer can be used for the laminate. Examples of layers include a web of fibrous material such as a woven web, nonwoven web, or any combination thereof. For example, at least one layer that is laminated on the nonwoven web is a second nonwoven web. In some embodiments, the process described in regard to FIGS. 2A and 2B can be utilized to create fiber-to-fiber bonds among loose fibers of the second nonwoven, thereby creating a layer of nonwoven web. In other embodiments, the process can be utilized to provide supplemental bonding to an already lightly bonded nonwoven web. Additionally, in some embodiments, the supplemental bonding can join the nonwoven web to a support structure. For example, the nonwoven web can have an initial bonded area of between about 10% and about 20% and can subsequently be bonded to a support layer (e.g., second nonwoven web) using the bond patterns of the subject invention. The resulting receiving component can have a bonded area higher than the initial bonded area.

The support layer may contain any suitable support layer known in the art. For example, the support layer can include films or nonwoven webs. Embodiments are contemplated where the receiving component is joined to a disposable absorbent article utilizing the bond patterns of the subject invention. For example, the receiving component can be joined to a backsheet of a disposable diaper.

One advantage of joining a receiving component to an underlying support layer utilizing the bond patterns of the subject invention is that, in some embodiments, no adhesive is required. For example, in certain embodiments, when using a calendering system as described in regard to FIGS. 2A and 2B, the bond pattern of the subject invention can be utilized to join a receiving component and a support layer without adhesive.

In certain embodiments, the initial bonded area of a receiving component may not be able to be measured. Specifically, in embodiments where the receiving component contains a nonwoven web having hydroentangled fibers or needle punched fibers, an initial bonded area may not be ascertainable. However, these nonwoven webs can still be utilized in a receiving component and can be joined to underlying support layers using the bonding patterns of the subject invention.

As mentioned previously, a receiving component constructed in accordance with the subject invention may contain the nonwoven web. In some embodiments, the nonwoven web may contain one layer of fibers. In other embodiments, the nonwoven web may contain more than one layer of fibers (e.g., the nonwoven web and a second layer such as a second nonwoven web). Any suitable second nonwoven web can be used. For example, a suitable second nonwoven may contain fibers made of polypropylene, polyethylene, polyester, nylon, cellulose, polyamide, or combinations of such materials. Fibers of one material or fibers of different materials or material combinations may be used in the nonwoven web and/or the second nonwoven. Exemplary second nonwoven materials include spunbond, spunbond meltblown spunbond (SMS), spunbond meltblown meltblown spunbond (SMMS), carded, meltblown, and the like. Particularly acceptable second nonwovens include high elongation carded (HEC) nonwovens and deep activation polypropylene (DAPP) nonwovens. Any process known in the art may be used to make the second nonwovens.

The second nonwoven may contain fibers that are bonded mechanically, including fibers that are needle punched or hydro entangled. Other suitable bonding processes for producing the suitable second nonwoven for use in the subject invention are spun bonding, thermally bonding, bonding by various types of chemical bonding such as latex bonding, powder bonding, and the like.

In certain embodiments, the basis weight of the second nonwoven can be in the range of about 10 g/m$^2$ to about 100 g/m$^2$ or any individual number within the range. In other embodiments, the basis weight of the second nonwoven can be in a range of about 25 g/m$^2$ to about 80 g/m$^2$. In yet other embodiments, the basis weight of the second nonwoven can be in a range of about 30 g/m$^2$ to about 50 g/m$^2$.

In some embodiments, the fiber of the second nonwoven may have a denier ranging from about 1 to about 10 or any individual number within the range. In some embodiments, the denier of the fibers can range from about 1 to about 8. In other embodiments, the denier of the fibers can range from about 1 to about 5. Additionally, in some embodiments, the second nonwovens can contain fibers made of polypropylene, polyethylene, polyolefins, bicomponent fibers, or any combination thereof.

The laminate can be formed by in-line lamination before bonding the above-mentioned nonwoven web containing the crimped composite fibers or out-line lamination after bonding the nonwoven web. When laminating by in-line lamination, it is desirable that a layer is put on the above-mentioned nonwoven web containing the crimped composite fibers before the bonding treatment and is laminated and combined by thermal fusion under the conditions as described above. Therefore, a material of nonwoven web that is laminated by in-line lamination can be any suitable polymer as long as it is thermally fused with the above-mentioned nonwoven web containing the crimped composite fibers.

When laminating by in-line lamination, it is desirable that the other layer (e.g., second layer) that is laminated with the nonwoven web of the subject invention is a layer of nonwoven web. Examples of layers of nonwoven web include a layer containing a spun-bonded nonwoven web, melt blown nonwoven web, carded nonwoven web, and the like. In one embodiment, the above-mentioned nonwoven webs that have different degrees of crimping can be the second layer and used for lamination.

Examples of polymers of the second nonwoven web include polyolefins, polyesters, polyamides, polyurethanes, etc. Examples of polyolefins include propylene, polyethylene, and mixtures thereof. From the standpoint of spinnability, heat resistance, and thermal fusion property with the above-mentioned nonwoven web containing the crimped composite fibers, polypropylene is preferred.

Polypropylenes that are similar to the first propylene polymer or the second propylene polymer contained in the above-mentioned crimped composite fibers can be used as the second layer. For example, when a melt blown second nonwoven web is used, it is desirable that polypropylenes having a melt-flow rate in the range of about 30 to about 3000 g/10 min, especially about 400 to about 1500 g/10 min, and a ratio of weight average molecular weight to number average molecular weight Mw/Mn in the range of about 2 to about 6.

In one embodiment, for the polyethylene, homopolymers of ethylene (either low pressure method or high pressure method may be used for production) and copolymers of ethylene and other α-olefins can be used as the second layer. Examples of α-olefins include α-olefins with about 3 to about 20 carbon atoms such as propylene, 1-butene, 1-pentene, 1-hexene, 1-octene, 1-decene, 3-methyl-1-butene, 3-methyl-1-pentene, 3-ethyl-1-pentene, 4-methyl-1-pentene, and 4-methyl-1-hexene. α-olefin may be used independently for copolymerization or two or more different types of α-olefins may be used in combination for copolymerization.

It is desirable that the polyethylene has a density in the range of about 880 to about 970 kg/m$^3$, especially in the range of about 910 to about 965 kg/m$^3$, and in the case of a melt blown nonwoven web, the melt flow rate is in the range of about 10 to about 400 g/10 min, especially in the range of about 15 to about 250 g/10 min. In one embodiment, it is desirable that a ratio of the weight average molecular weight to number average molecular weight, Mw/Mn, is in the range of about 1.5 to about 4.

Examples of polyesters include aromatic polyesters having excellent strength, rigidity, etc., and biodecomposable aliphatic polyesters. Examples of aromatic polyesters include polyethylene terephthalate, polytrimethylene terephthalate, polytetramethylene terephthalate, etc. Examples of aliphatic polyesters include polycondensates of a poly-carboxylic acid (e.g., malonic acid, succinic acid, glutaric acid, adipic acid, sebacic acid, dodecanoic acid, malic acid, tartaric acid, citric acid, etc.) and a poly-alcohol (e.g., ethylene glycol, propylene glycol, butanediol, hexanediol, glycerol, trimethylolpropane, etc.); ring opening polymers (e.g., lactide and caprolactone, etc.); and polycondensates of hydroxy acid (e.g., lactic acid, hydroxybutyric acid, hydroxyvaleric acid, etc.); and the like.

When the nonwoven web laminate is produced off-line, the other layer (e.g., second layer) that can be laminated onto the above-mentioned nonwoven web containing the crimped composite fibers is not especially limited, and can be a layer containing a knitted fabric, woven fabric, nonwoven fabric, film, etc. Examples of methods for laminating include a thermal fusion process such as embossing finish, ultrasonic fusion, etc.; a mechanical webbing method such as needle punching, water jetting, etc.; adhesion using a hot melt adhesive, etc.; extrusion lamination in the case of a film, etc.; and the like.

The nonwoven web for a receiving fastener component in accordance with the subject invention has sufficient fastening strength in all of peel strength, repeat peel strength, and tensile shear strength, and at the same time, high mechanical strength in both of the MD and CD. Also, the nonwoven web has high bulkiness and softness as well as excellent spinnability and excellent fuzzing resistance. Therefore, the nonwoven web can be used for a fastener component for a paper diaper, incontinence product, operation gown, and the like, as described in detail below.

A fastening system containing the nonwoven web in accordance with the subject invention may be incorporated into a variety of consumer and commercial goods that may benefit from having a receiving component which contains a bond pattern constructed in accordance with the subject invention. In any of the embodiments described herein, the receiving component may be a separate element added to the commercial good. For example, the receiving member may be a discrete structure joined to any component (e.g., a topsheet, an absorbent core, a backsheet, a fastening system, a side panel, a cuff, etc.) of an absorbent article or other commercial good (e.g., a wrap, a medical product, etc.). Alternatively, the receiving component may be constructed as part or all of any element of the commercial good or fastener. For example, the receiving component may be constructed as part or all of any component (e.g., a topsheet, an absorbent core, a backsheet, a fastening system, a side panel, a cuff, etc.) of an absorbent article or other commercial good (e.g., a wrap, a medical product, etc.). Further, receiving component may be disposed in any suitable location on or in the commercial good or fastener. For example, the receiving component may be disposed on an outer-facing surface of, wearer-facing surface of, or contained within the commercial good or fastener. For the sake of explanation, the receiving component of the subject invention is discussed in the context of disposable diapers, although additional contexts are also applicable.

Figure 7A:
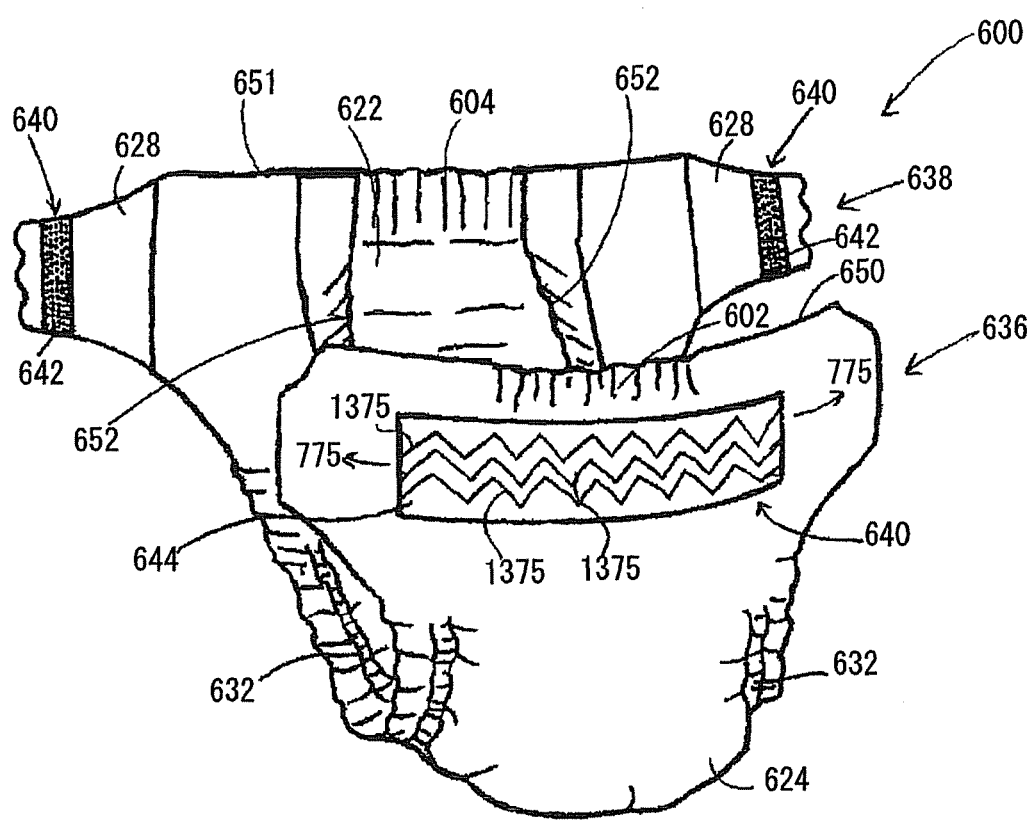
FIG. 7A is a perspective view showing a disposable absorbent article containing a nonwoven web in accordance with the subject invention.
Figure 7B:
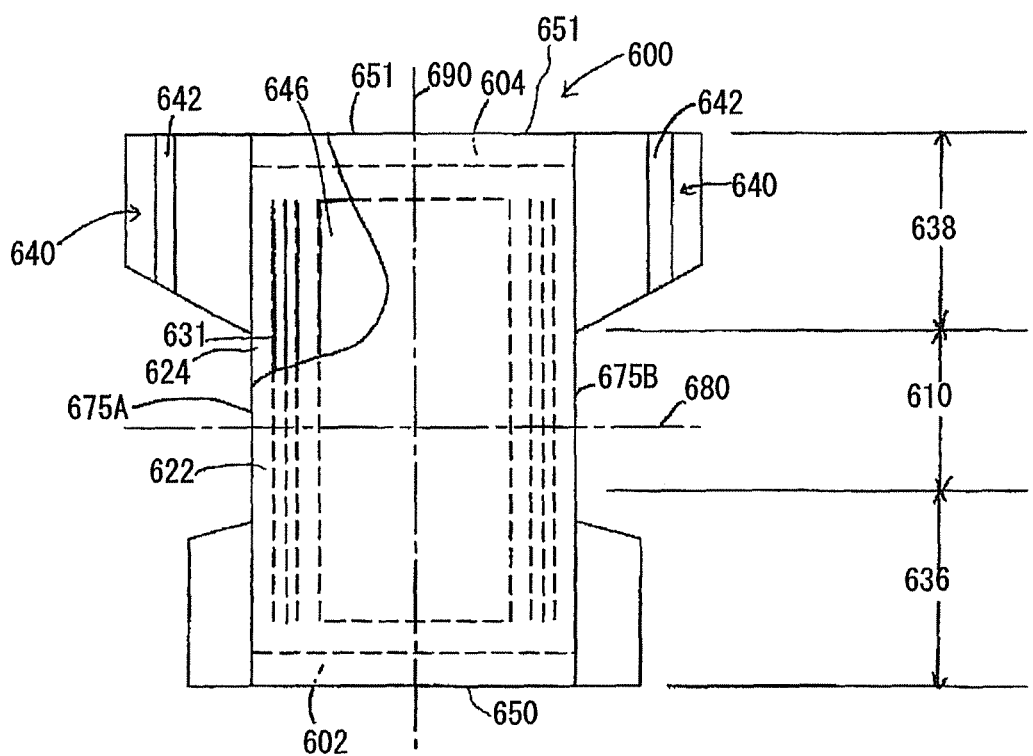
FIG. 7B is a plan view showing the disposable absorbent article of FIG. 7A in a flattened-out uncontracted state.

As shown in FIGS. 7A and 7B, a disposable absorbent article 600 may contain a liquid pervious topsheet 622 and a backsheet 624 joined to at least a portion of the topsheet 622. The disposable absorbent article 600 further contains an absorbent core 646 positioned between the topsheet 622 and the backsheet 624. The disp o sable absorbent article 600 may further contain side panels 628, outer cuffs 632, inner cuffs 652, and waist features 630.

A portion of the periphery of the disposable absorbent article 600 can be defined by the longitudinal edges 675A and 675B; the first waist edge 650, and the second waist edge 651. The longitudinal edges 675A and 675B may run generally parallel to a longitudinal centerline 690 of the disposable absorbent article 600. The first waist edge 650 and the second waist edge 651 may run generally parallel to a lateral centerline 680 of the disposable absorbent article 600. The disposable absorbent article 600 may further contain elastic leg features 631 which can be disposed adjacent to the longitudinal edges 675A and 675B.

The disposable absorbent article 600 may further contain a first waist member 602 and a second waist member 604. The first waist member 602 and/or the second waist member 604 can be elastically extensible. As shown, in some embodiments, the first waist member 602 can be disposed adjacent the first waist edge 650. In some embodiments, the second waist member 604 can be disposed adjacent to the second waist edge 651. Generally, the first waist member 602 and/or the second waist member 604 can be under tension prior to joining to the disposable absorbent article 600. So, upon release of at least a portion of the tension applied to the first waist member 602 and/or the second waist member 604, a portion of the disposable absorbent article 600 joined thereto can corrugate. This corrugation of the disposable absorbent article 600 can allow the first waist member 602 and/or the second waist member 604 and the disposable absorbent article 600 to expand and contract about the waist of a wearer, thereby providing more comfort and improved fit to a wearer. Examples of suitable waist members 602 and/or 604 include those described in U.S. Pat. No. 4,515,595, U.S. Pat. No. 5,151,092, and U.S. Pat. No. 5,221,274, all of which are hereby incorporated by reference in for this regard. Although disposable diapers are generally constructed so as to have two elastic waist features, one positioned in a first waist region and one-positioned in a second waist region, diapers can be constructed with a single elastic waist feature.

The disposable absorbent article 600 may further contain outer cuffs 632 and inner cuffs 652 to improve containment of liquids and other body exudates. Each elasticized outer cuff 632 may include several different embodiments for reducing the leakage of body exudates in the leg regions. Outer cuffs 632 and inner cuffs 652 are further described in U.S. Pat. No. 3,860,003; U.S. Pat. No. 4,909,803; and U.S. Pat. No. 4,695,278, all of which are hereby incorporated by reference in for this regard.

As stated previously, the disposable absorbent article may further contain a pair of side panels 628. As shown in FIG. 7B, the side panels 628 can extend outward from the first longitudinal edge 675A and the second longitudinal edge 675B of the disposable absorbent article 600. In some embodiments, the side panels 628 can be joined to the disposable absorbent article 600 in the second waist region 638, and in some embodiments, the side panels 628 can be joined to the disposable absorbent article 600 in the first waist region 636. Alternatively, in some embodiments, the disposable absorbent article 600 may contain a pair of side panels which are disposed in the second waist region 638 and a pair of side panels which are disposed in the first waist region 636. In some embodiments, the side panels 628 can form a portion of the leg openings when the disposable absorbent article 600 is fastened. The side panels 628 can form a portion of the leg openings which would be disposed on an outer surface of a leg of a wearer. A crotch region 610 of the disposable absorbent article 600 in conjunction with the first waist region 636 and the second waist region 638 can form a portion of the leg openings which would be disposed on an inner surface of the leg of the wearer. In some embodiments, the side panels 628 can be elastically extensible.

The disposable absorbent article 600 further contains a fastening system 640 which joins at least a portion of a first waist region 636 with at least a portion of a second waist region 638, preferably to form leg and waist openings. The fastening system 640 also works with the waist members (s) 602 and/or 604 to maintain lateral tension in order to keep the disposable absorbent article 600 in place about the waist of the wearer. The fastening system 640 may contain engaging components 642 which, in some embodiments, can be disposed on the side panels 628. The fastening system 640 may further contain a receiving component 644 which, in some embodiments, is disposed in the first waist region 636.

Figure 7C:
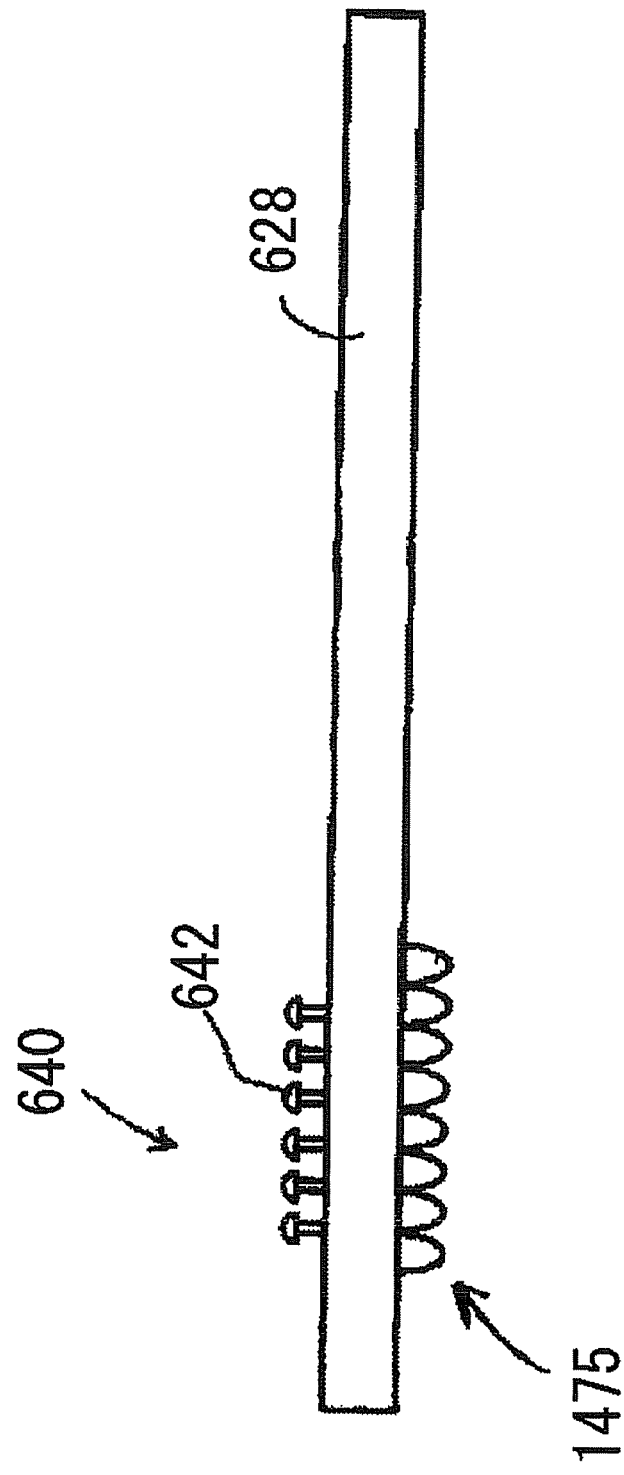
FIG. 7C is an elevation view showing another embodiment of a side panel of the disposable absorbent article of FIG. 7A.

As shown in FIG. 7C, in other embodiments, the fastening system 640 can include a plurality of fastening components on the side panels 628. For example, as shown, the side panel 628 may contain the engaging component 642 which, in some embodiments, can include a plurality of engaging elements. Additionally, in some embodiments, the side panel 628 may further contain a receiving component 1475 which is disposed opposite of the engaging component 642. One advantage of this arrangement is that the engaging component 642 can engage the receiving component 644 (shown in FIG. 7A) which is joined to the first waist region 636 or can join to the receiving component 1475 of the other side panel 628.

As shown in FIG. 7A, the receiving component 644 is disposed on the disposable absorbent article 600 such that the overlap of the bond lines 1375 is generally perpendicular to the primary direction of shear 775. As shown in FIG. 7A, the primary direction of shear 775 is an expected in use force which typically occurs once the disposable absorbent article 600 is in a fastened state. In some embodiments, the receiving component 644 can be disposed adjacent the first waist edge 650 in the first waist region 636 on an outer-facing surface of disposable absorbent article 600. In other embodiments, the receiving component 644 can be disposed adjacent the second waist edge 651 in the second waist region 638. In this embodiment, the engaging elements 642 can be disposed adjacent the first waist region 636. In some embodiments, receiving components 644 can be disposed on the side panels 628 and the engaging component can be disposed in the first waist region 636. In some embodiments, the receiving component 644 may contain a plurality of discrete elements.

Any suitable engaging element 642 can be used in the subject invention. An example of a suitable engaging element 642 contains hook fastening material. The hook fastening material can mechanically engage fibrous elements of the receiving element 644 so as to provide a secure closure. A hook fastening material according to the subject invention may be manufactured from a wide range of materials. Suitable materials include nylon, polyester, polypropylene, or any combination of these materials, or other materials as are known in the art.

A suitable hook fastening material contains a number of shaped engaging elements projecting from a backing such as the commercially available material designated Scotchmate™ brand No. FJ3402 available from Minnesota Mining and Manufacturing Company, St. Paul, Minn. Alternatively, the engaging elements may have any shape such as hooks, "T's," mushrooms, or any other shape as are well known in the art. An exemplary hook fastening material is described in U.S. Pat. No. 4,846,815, which is hereby incorporated by reference in for this regard. Another suitable hook fastening material contains an array of prongs formed of thermoplastic material. Hot melt adhesive thermoplastics, in particular polyester and polyamide hot melt adhesives, are particularly well suited for forming the prongs of the hook fastening material. The prongs, in some embodiments, can be manufactured using a modified gravure printing process by printing the thermoplastic material in its molten state onto a substrate in discrete units, severing the material in a manner that allows stretching of a portion of the thermoplastic material prior to severance, and allowing the stretched molten material to "freeze" resulting in prongs. This hook fastening material and methods and apparatus for making such a hook fastening material are more fully detailed in European Patent Application 0 381 087, which is hereby incorporated by reference in for this regard.

The fastening system 640 may be the primary fastening system for joining the first and second waist regions 636 and 638. However, the fastening system 640 may be used alone or in conjunction with other fastening means such as tab and slot fasteners, tape fasteners, snaps, buttons, and the like to provide different fastening characteristics. For example, the fastening system 640 may provide the disposable absorbent article 600 with a disposal means for fastening the disposable absorbent article 600 in a configuration convenient for disposal. Further, secondary fastening means may provide the disposable absorbent article 600 with a means for adjusting fit or may increase the strength of the connection between the first waist region 636 and the second waist region 638.

The fastening system 640 can be prefastened in a package such that a caregiver or wearer may pull on the disposable absorbent article 600 when removed from the package. Alternatively, the fastening system 640 can be unfastened in the package such that the caregiver or wearer fastens the fastening system 640 while donning the disposable absorbent article 600. In yet another embodiment, a package may contain both prefastened and unfastened disposable absorbent articles 600 for the convenience of the caregiver or the wearer.

Figure 8A:
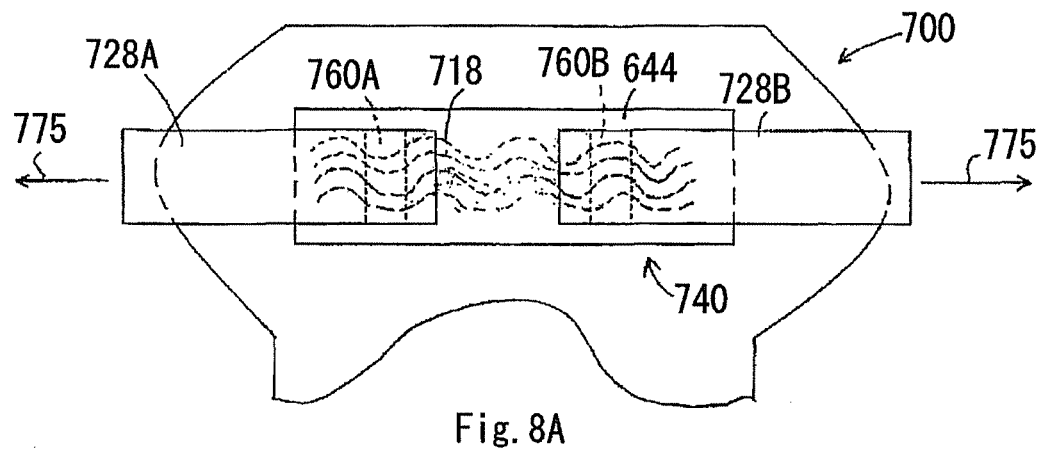
FIG. 8A is an elevation view showing a portion of the disposable absorbent article of FIG. 6 having its fastening system in a fastened state.

As shown in FIG. 8A, a disposable absorbent article 700 containing a fastening system 740 is shown. The fastening system 740 contains a first engaging component 760A disposed on a first side panel 728A and a second engaging component 760B disposed on a second side panel 728B. The first engaging component 760A and the second engaging component 760B can engage the receiving component 644 when fastened.

The receiving component 644 may contain a plurality of bond lines 718 created in accordance with the subject invention. Each of the plurality of bond lines 718 may contain hills and valleys. As mentioned previously, the receiving component 644 can be disposed on the disposable absorbent article 700 such that the overlap between the bond lines is generally perpendicular to the primary direction of shear 775. So, receiving components of the subject invention constructed similar to the receiving component 100 (shown in FIGS. 1B and 3) can be disposed on the disposable absorbent article 700 such that the lateral axis 162 (shown in FIGS. 1B and 3) of the receiving component is generally parallel to the primary direction of shear 775. Alternatively, receiving components of the subject invention constructed similar to the receiving component 1000 (shown in FIG. 6) can be disposed on the disposable absorbent article 700 such that the longitudinal axis 1060 of the receiving component is generally parallel to the primary direction of shear 775.

The primary direction of shear 775 is defined by the in use forces. Specifically, when the disposable absorbent article 700 is in a fastened state, the first side panel 728A and the second side panel 728B exert a force on the receiving component 644. The force can be caused, in part, by the elastomeric material of the side panels, if they are elastically extensible. Additionally, the shear forces may be caused by user or caregiver during application of the disposable absorbent article 700.

Figure 8B:
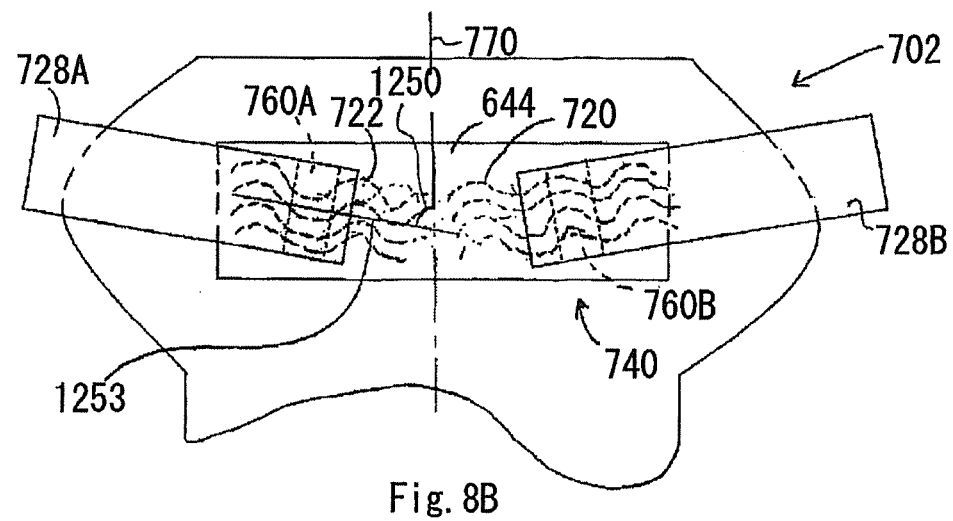
FIG. 8B is an elevation view showing a portion of the disposable absorbent article of FIG. 7 having its fastening system in a fastened state, wherein a receiving component of the fastening system is disposed on the disposable absorbent article to provide a visual alignment aid.

As shown in FIG. 8B, a disposable absorbent article 702 containing a fastening system 740 is shown. Similar to the disposable absorbent article above, the first engaging component 760A and the second engaging component 760B can engage the receiving component 644 when fastened. The receiving component 644 may contain a first plurality of bond lines 722 and a second plurality of bond lines 720. A portion of each of the first plurality of bond lines 722 overlaps a portion of each adjacent bond line. Similarly, a portion of each of the second plurality of bond lines 720 overlaps a portion of each adjacent bond line.

The first plurality of bond lines 722 may be angled such that they can provide a visual signal to a wearer of where to fasten the first engaging component 760A. Additionally, the second plurality of bond lines 720 may be angled such that they can provide a visual signal to a wearer of where to fasten the second engaging component 760B.

In some embodiments, the fastening angles 1250 can be in a range from between about 0 degrees to about 45 degrees or any individual number within that range. In other embodiments, the fastening angle 1250 can be between about 10 degrees and about 25 degrees. In yet other embodiments, the fastening angle 1250 can be between about 15 degrees and about 20 degrees.

The fastening angle 1250 of the first plurality of bond lines 722 can be determined by performing straight line approximations for each of the bond lines within bond pattern of the first plurality of bond lines 722. A bond line can be considered to be a part of the first plurality of bond lines 722 if a portion of that bond line overlaps any portion of another bond line within the first plurality of bond lines 722. The straight line approximations for each of the bond lines within the first plurality of bond lines 722 can be averaged to determine a first orientation line 1253 for the first plurality of bond lines 722. The intersection between the first orientation line 1253 and a longitudinal axis 770 of the disposable absorbent article 702 defines the fastening angle 1250. The same analysis can be performed for the second plurality of bond lines 720.

Disposable absorbent articles may contain many components, elements, members, etc. and can be constructed in a variety of manners. For example, the topsheet 622 (shown in FIG. 6) and the backsheet 624 (shown in FIG. 6) can have length and width dimensions generally larger than those of the absorbent core 626 (shown in FIG. 6). The topsheet 622 (shown in FIG. 6) and the backsheet 624 (shown in FIG. 6) can extend beyond the edges of the absorbent core 626 (shown in FIG. 6), thereby forming the periphery of the disposable absorbent article 600 (shown in FIG. 6). The topsheet 622 (shown in FIG. 6), the backsheet 624 (shown in FIG. 6), and the absorbent core 626 (shown in FIG. 6) may include many different materials and may be assembled in a variety of well known configurations, exemplary diaper materials and configurations are described generally in U.S. Pat. No. 3,860,003, U.S. Pat. No. 5,151,092, and U.S. Pat. No. 5,221,274, all of which are hereby incorporated by reference in for this regard.

Any topsheet compatible with the subject invention which is known in the art can be used in the subject invention. A suitable material for a topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. As an example, a material suitable for use in a topsheet contains a web of staple-length polypropylene fibers is manufactured by Veratec, Inc., a Division of International Paper Company, of Walpole, Mass. under the designation P-8.

Some examples of suitable topsheets are described further in U.S. Pat. No. 3,929,135; U.S. Pat. No. 4,324,246; U.S. Pat. No. 4,342,314; U.S. Pat. No. 4,463,045; U.S. Pat. No. 5,006,394; U.S. Pat. No. 4,609,518; U.S. Pat. No. 4,629,643, all of which are hereby incorporated by reference in for this regard.

Any portion of the topsheet may be coated with a lotion as is known in the art. Examples of suitable lotions include those described in U.S. Pat. No. 5,607,760; U.S. Pat. No. 5,609,587; U.S. Pat. No. 5,635,191; U.S. Pat. No. 5,643,588; U.S. Pat. No. 5,968,025; U.S. Pat. No. 6,716,441; and PCT Publication No. WO 95/24173, all of which are hereby incorporated by reference in for this regard.

Further, the topsheet may be fully or partially elastically extensible or may be foreshortened so as to provide a void space between the topsheet and the absorbent core. Exemplary structures including elasticized or foreshortened topsheets are described in more detail in U.S. Pat. No. 4,892,536; U.S. Pat. No. 4,990,147; U.S. Pat. No. 5,037,416; and U.S. Pat. No. 5,269,775, all of which are hereby incorporated by reference in for this regard.

A suitable backsheet for use in the disposable absorbent article of the subject invention may contain a laminated structure. For example, as previously discussed, the backsheet may contain a first backsheet layer and a second backsheet layer (see items 241 and 242 of FIG. 2C). The second backsheet layer can be impervious to liquids (e.g., urine) and contain a thin plastic film such as a thermoplastic film having a thickness, for example, of about 0.012 mm (0.5 mils) to about 0.051 mm (2.0 mils). Suitable backsheet films include those manufactured by Tredegar Corporation, based in Richmond, Va., and sold under the trade name CPC2 film. Either the first backsheet layer and/or the second backsheet layer may include breathable materials which permit vapors to escape from the pull-on garment while still preventing exudates from passing through the backsheet. Suitable breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746; U.S. Pat. No. 5,938,648; U.S. Pat. No. 5,865,823; and U.S. Pat. No. 5,571,096, all of which are hereby incorporated by reference in for this regard.

The backsheet, or any portion thereof, may be elastically extensible in one or more directions. In one embodiment, the backsheet may contain a structural elastic-like film ("SELF") web. A structural elastic-like film web is an extensible material that exhibits an elastic-like behavior in the direction of elongation without the use of added elastic materials and is described in more detail in U.S. Pat. No. 5,518,801, which is hereby incorporated by reference in for this regard. In alternate embodiments, the backsheet may contain elastic films, foams, strands, or combinations of these or other suitable materials with nonwovens or synthetic films.

A suitable absorbent core for use in the subject invention may contain any absorbent material which is generally compressible, conformable, non-irritating to the wearer's skin, and capable of absorbing and retaining liquids such as urine and other certain body exudates. In addition, the configuration and construction of the absorbent core may also be varied (e.g., the absorbent core(s) or other absorbent structure(s) may have varying caliper zones, hydrophilic gradient(s), a superabsorbent gradient(s), or lower average density and lower average basis weight acquisition zones; or may contain one or more layers or structures). Suitable exemplary absorbent structures for use as the absorbent core are described in U.S. Pat. No. 4,610,678; U.S. Pat. No. 4,673,402; U.S. Pat. No. 4,834,735; U.S. Pat. No. 4,888,231; U.S. Pat. No. 5,137, 537; U.S. Pat. No. 5,147,345; U.S. Pat. No. 5,342,338; U.S. Pat. No. 5,260,345; U.S. Pat. No. 5,387,207; and U.S. Pat. No. 5,625,222, all of which are hereby incorporated by reference in for this regard.

The backsheet may be joined to the topsheet, the absorbent core, or any other element of the disposable absorbent article by any attachment means known in the art. For example, the attachment means may include a uniform continuous layer of adhesive, a patterned layer of adhesive, or an array of separate lines, spirals, or spots of adhesive. Some suitable attachment means are disclosed in U.S. Pat. No. 4,573,986; U.S. Pat. No. 3,911,173; U.S. Pat. No. 4,785,996; and U.S. Pat. No. 4,842,666, all of which are hereby incorporated by reference in for this regard. Examples of suitable adhesives are manufactured by H. B. Fuller Company of St. Paul, Minn. and marketed as HL-1620 and HL-1358-XZP. Alternatively, the attachment means may contain heat bonds, pressure bonds, ultrasonic bonds, dynamic mechanical bonds, or any other suitable attachment means or combinations of these attachment means as are known in the art.

Various sublayers may be disposed between the topsheet and the backsheet. The sublayer may be any material or structure capable of accepting, storing or immobilizing bodily exudates. Thus, the sublayer may include a single material or a number of materials operatively associated with each other. Further, the sublayer may be integral with another element of the pull-on disposable absorbent article or may be one or more separate elements joined directly or indirectly with one or more elements of the disposable absorbent article. Further, the sublayer may include a structure that is separate from the absorbent core or may include or be part of at least a portion of the absorbent core.

Suitable exemplary materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures containing a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and, more specifically, having pores greater than about 1.0 mm in diameter.) One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. No. 6,680,422 and U.S. Pat. No. 5,941,864, both of which are hereby incorporated by reference in for this regard. Further, the sublayer, or any portion thereof, may include or be coated with a lotion or other known substances to add, enhance or change the performance or other characteristics of the element.

Embodiments of the subject invention may also include pockets for receiving and containing waste, spacers which provide voids for waste, barriers for limiting the movement of waste in the article, compartments or voids which accept and contain waste materials deposited in the pull-on disposable absorbent article, and the like, or any combinations thereof. Examples of pockets and spacers for use in absorbent products are described in U.S. Pat. No. 5,514,121; U.S. Pat. No. 5,171,236; U.S. Pat. No. 5,397,318; U.S. Pat. No. 5,540,671; U.S. Pat. No. 6,168,584; U.S. Pat. No. 5,306,266; and U.S. Pat. No. 5,997,520, all of which are hereby incorporated by reference in for this regard. Examples of compartments or voids in an absorbent article are disclosed in U.S. Pat. No. 4,968,312; U.S. Pat. No. 4,990,147; U.S. Pat. No. 5,062,840; and U.S. Pat. No. 5,269,755, all of which are hereby incorporated by reference in for this regard. Examples of suitable transverse barriers are described in U.S. Pat. No. 5,554,142; PCT Patent WO 94/14395; and U.S. Pat. No. 5,653,703, all of which are hereby incorporated by reference in for this regard. Examples of other structures suitable for management of low viscosity feces are disclosed in U.S. Pat. No. 5,941,864; U.S. Pat. No. 5,977,430; and U.S. Pat. No. 6,013,063, all of which are hereby incorporated by reference in for this regard.

Embodiments of the subject invention may include acquisition/distribution layers which can be configured to distribute moisture from a wetness event to moisture responsive members within the disposable absorbent article. Examples of suitable acquisition/distribution layers are described in U.S. Pat. No. 5,460,622, U.S. Patent Application Publication No. 2005/0027267, and U.S. Patent Application Publication No. 2005/009173, all of which are hereby incorporated by reference in for this regard. Embodiments of the subject invention may include a dusting layer which is well known in the art. Examples of suitable dusting layers are discussed in U.S. Pat. No. 4,888,231, which is hereby incorporated by reference in for this regard.

EXAMPLES

The subject invention is further explained specifically with examples below, but the subject invention is not limited to the examples shown below. In the examples and comparative examples shown below, fastening strength (tensile shear strength and peel strength), mechanical strength (tensile strength in MD and CD), basis weight, etc., were measured according to the methods described below.

Test Methods:
(1) Fastening Strength

The two evaluations as described below, "tensile shear strength" and "peel strength" were conducted. The larger the values of the two evaluations are, the more desirable the strength.

The tensile shear strength was measured by the following procedure. The tensile shear strength was measured in accordance with JIS L 3416 except the procedure as described below.

Ten test pieces (MD 50 mm×CD 70 mm) were prepared from a nonwoven web for a receiving fastener component. Each of the test pieces was attached to a metal plate (material: SUS304, size: 50 mm×100 mm, thickness: 1 mm) by a two-sided tape so that the CD of the test piece conforms to the longitudinal direction of the metal plate.

A Mushroom tape (male component, MD 25 mm×CD 13 mm) was attached to the end of a copy paper (strip of paper) of 25 mm in width×100 mm by a two-sided tape. The hook material was made of polypropylene with hooks having a mean height of 0.4 mm, a mean end size of 0.2 mm by 0.3 mm, and an approximate density of 220 hooks/cm$^2$.

The strip of paper was put on the center of the test piece with the surface having the Mushroom tape down. At this time, the CD of the test piece conformed to the CD of the Mushroom tape.

A metal roller (50 mm in width, 5 kg in weight) was put on the strip of paper and moved back and forth through the Mushroom tape so that the Mushroom tape was fastened to the test piece.

The test piece and strip of paper were attached to a chuck of a tensile testing machine in a manner that the tensile direction conformed to the CD of the test piece, the end of the metal plate was upper, and the end of the copy paper was lower, tensile shear strength (N/25 mm) until the test piece was peel off from the strip of paper was measured with an operation of a distance between the chucks of 75 mm and a velocity of 300 mm/min, and an average of maximal values (peak values) in each measurement for the 10 test pieces was obtained as a tensile shear strength.

Peel strength and repeat peel strength.

The peel strength and repeat peel strength were measured by the following procedure. The peel strength and repeat peel strength were measured in accordance with JIS L 3416 except the procedure as described below.

Ten test pieces (MD 50 mm×CD 100 mm) were prepared from a nonwoven web for a receiving fastener component. The Mushroom tape as employed in measuring the tensile shear strength was attached to the end of a copy paper as employed in measuring the tensile shear strength by a two-sided tape.

The strip of paper was put on the center of the test piece with the surface having the Mushroom tape down. At this time, the CD of the test piece conformed to the CD of the Mushroom tape. Also, to determine the location of the strip of the paper, a mark was applied on the test piece.

A metal roller (50 mm in width, 5 kg in weight) was put on the strip of paper and moved back and forth through the Mushroom tape so that the Mushroom tape was fastened to the test piece.

The end portion of the test piece that was not attached to the strip of paper was held back from the Mushroom tape at 180 degrees.

The test piece and strip of paper were attached to a chuck of a tensile testing machine in a manner that the tensile direction conformed to the CD of the test piece, the end of the test piece was upper, and the end of the strip of paper that was held back was lower, peel strength (N/25 mm) until the test piece was peel off from the strip of paper was measured with an operation of a distance between the chucks of 75 mm and a velocity of 300 mm/min, and an average of maximal values (peak values) in each measurement for the 10 test pieces was obtained as a peel strength.

After conducting the above mentioned procedure at two times with fastening the strip of paper having the Mushroom tape to the test piece at the marked location as used in the above measurement, a peel strength on the third measurement was obtained as a repeat peel strength.

(2) Mechanical Strength

The mechanical strength was measured by the following procedure. The mechanical strength was measured in accordance with JIS L 1906 except the procedure as described below.

Ten test pieces (MD 25 mm×CD 200 mm) were prepared from a nonwoven web for a receiving fastener component.

Each of the test pieces was subjected to a tensile measurement using a tensile testing machine (Instron 5564 available from Instron Corp.) under the conditions of a distance between the chucks of 100 mm and a tensile velocity of 100 mm/min. Maximum load values (N/25 mm) until the test piece was ruptured were measured and maximum tensile strength was obtained by calculating an average of the maximum load values.

(3) Basis Weight

The basis weight was measured by the following procedure. The basis weight was measured in accordance with JIS L 1906 except the procedure as described below.

Before forming a laminate material, each layer of nonwoven web was formed on layer to layer independently, and a single layer was formed. While forming the layer, the conditions for forming the layer was controlled to provide for a predetermined basis weight. Ten test pieces of 100 mm×100 mm were prepared from each layer, and a basis weight was a value in terms of $g/m^2$.

A laminate was formed under conditions under which each of the layers was formed, the above mentioned basis weight was referred to as a basis weight of each of the layers. And, a sum of each basis weight of the layers was referred to as a basis weight of the laminate.

(4) Number of Crimps

The number of crimps was measured by the following procedure. The number of crimps was measured in accordance with JIS L1015 except the procedure described below.

Sectioning lines with a spatial distance of 25 mm were drawn on a piece of glossy paper with a smooth surface. A fiber was removed carefully from a nonwoven web prior to a thermal compression treatment by an embossing roll such that crimps remain intact, and the both ends of each fiber were attached onto the piece of paper by an adhesive in the manner that the fiber had looseness of 25±5% to the spatial distance.

Each of the test pieces was applied to clamps of a crimping tester (device name: Torsion balance available from Asano Kikai Seisakusho Kabushiki-kaisha), and the distance between the clamps (spatial distance) (mm) was read during the initial load (0.18 mN×displayed tex number) was applied after cutting the piece of paper.

The number of crimps at this time was counted, the number obtained was then converted into the number of crimps per distance of 25 mm, and a mean value of 20 times was obtained. The number of crimps was obtained as the total peaks and valleys were counted and divided by two.

(5) Thickness (Bulkiness)

Five test pieces (100 mm×100 mm) were prepared from a nonwoven web for a receiving fastener component. The thickness of any three portions of the nonwoven was measured using a constant-pressure thickness meter (manufactured from Ozaki Seisakusho Kabushiki-kaisha). A diameter of a probe was 16 mm, a load was 3.6 $g/cm^2$, readings were recorded at 30 seconds±5 seconds after the probe completely contacted the test piece, and thickness (bulkiness) was obtained by calculating a mean value of five test pieces.

(6) Weight Ratio of First and Second Propylene Polymers that are Contained in a Composite Fiber A weight ratio of propylene polymers in a composite fiber was measured by the following procedure. One composite fiber was removed from a nonwoven web. The fiber was analyzed by TREF (Temperature Rising Elution Fractionation) method using CFC (Cross Fractionation Chromatograph) T-150A (manufactured by Mitsubishi Chemicals Corporation). The following conditions were used.

Detector: Infrared spectrometer 1ACVF (manufactured by Miran), 3.42 μm, 135° C.
TREF column: CFC column, inner diameter of 4 mm, length of 150 mm
Eluent: o-dichlorobenzene (ODCB)
Flow rate: 1.0 mL/min.
Concentration of sample: 30 mg/10 mL-ODCB
Sample volume: 500 μL Time for cooing temperature: Cooling a sample from 135° C. to 0° C. in 135 minutes, then holding the sample at 0° C. for 60 minutes Elution fraction: 0, 20, 40, 50, 60, 65, 70, 75, 80, 83, 86, 89, 92, 95, 98, 101, 104, 106, 108, 110, 112, 114, 116, 118, 120, 122, 125, 130, and 135° C.

Figure 10:
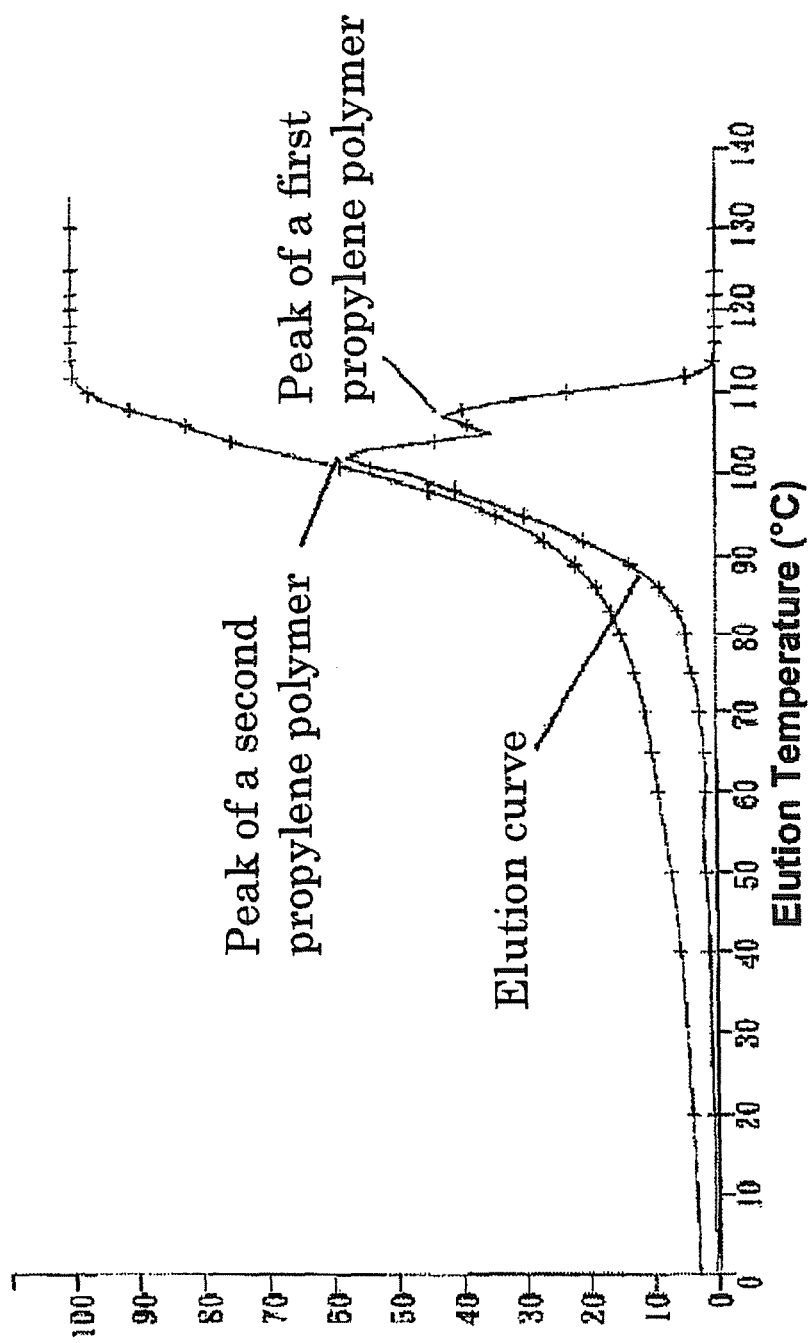
FIG. 10 illustrates an exemplary elution curve of a first propylene polymer and a second propylene polymer in accordance with the subject invention.

An exemplary elution curve is shown in FIG. 10. The curve indicates two peaks where each of the two peaks is based on the first propylene polymer and second propylene polymer, respectively. The area under the curve was calculated by integration of the curve and the area was divided into two areas by a perpendicular line at the valley between the two peaks.

A weigh ratio of the first propylene polymer to the second propylene polymer was obtained by calculating a ratio of the area under the peak of the first propylene polymer to the area under the peak of the second propylene polymer. A weight ratio of the first propylene polymer to the second propylene polymer was 21/79 calculated according to the elution curve shown in FIG. 10.

(7) Bonded Area of a Receiving Component

Sample Preparation

1. Enough representative absorbent articles are selected from the retail packaging of the absorbent article to conduct all required tests. The receiving components of each of the absorbent articles are removed from the articles. Suitable methods include cutting the receiving components off of the articles.
2. Each sample is allowed to equilibrate in a controlled environment. The environmental parameters are 22 degrees C.±2 degrees C., 50% Relative Humidity±10% Relative Humidity. Samples are placed in these conditions at least 24 hours prior to testing.
3. Secure a sample to a flat surface. The sample is secured to the flat surface such that the sample is completely disposed on the flat surface. The sample is secured to the flat surface using tape such as Scotch Removable Magic Tape™ manufactured by 3M™.
4. Identify the bond zone in accordance with the description of the bond zone described herein.
5. Identify the sweep regions within the bond zone in accordance with the description of the sweep regions described herein. Each of the sweep regions has a length which is equal to the contact area between the calendering rolls. Each of the sweep regions has a width which is equal to the width of the web the receiving component is produced on.
6. Measure the area bonded within each sweep region, and record the sweep region bonded areas as Bi, where i=1 to n with n being the total number of sweep regions. The bonded area is measured to the nearest 0.01 mm$^2$.
7. Measure the total area of each sweep region, and record the total sweep region area Si, where i=1 to n with n being the total number of sweep regions. The total area is measured to the nearest 0.01 mm$^2$.
8. From the data collected, calculate:
a) Bond Ratio:
  i) Identify the sweep region having the smallest bond area, record as Bi,min.
  ii) Identify the sweep region having the largest bond area, record as Bi,max.
  iii) Calculate the Bond Ratio=Bi,max/Bi,min.
b) % Bonded Area in each Sweep Region:
  i) Percent Bonded area for each sweep region=100*Bi/Si.
c) Overall % Bonded Area:
  i) Calculate cumulative bonded area, Bt=sum of Bi, where i=1 to n.
  ii) Calculate cumulative total area, St=sum of Si, where i=1 to n.
  iii) Overall Percent Bonded Area=100*Bt/St.

As stated previously, the areas may be measured using straight-line measures and geometric/trigonometric relationships. Alternatively, computerized image analysis may be used for more complex bond line patterns.

Example 21

A web containing a side-by-side composite fiber (fiber size of 2.5 denier) with a weight ratio of 20/80 was formed by composite hot-melt spinning via a spun-bonding method using a polypropylene homopolymer having a melting point of 162° C. and MFR=60 g/10 min (according to ASTM D1238, the measurement was conducted at a temperature of 230° C. and under load of 2.16 kg. The same conditions applies below unless otherwise specified.) and a propylene-ethylene random copolymer having a melting point of 142° C. and MFR=60 g/10 min. At this time, the forming conditions were controlled to provide a final basis weight of a nonwoven web of 45 g/m$^2$. The number of crimps of the fiber was 25 crimps/25 mm.

(Preparation and Evaluation of a Nonwoven Web for a Receiving Fastener Component)

A nonwoven web for a receiving fastener component having a basis weight of 45 g/m$^2$ was formed by passed the resultant web between an embossing roll having a surface engraved with a pattern shown in FIG. 3B and a roll having a smooth surface, and being subjected to a thermal compression treatment. In this case, the temperatures of both the embossing roll and smooth roll were 125° C. and the line pressure was 30 N/mm.

In the pattern shown in FIG. 3B, $W_1$=11.5 mm, $W_2$=9.3 mm ($W_1/W_2$=1.2), $W_3$=3.2 mm, $W_4$=1.0 mm, and the embossed area ratio was 24%. Furthermore, a part of the unit pattern is contained inside the triangle formed by adjacent three contact points of the first diagonal line and the second diagonal line in the unit pattern, the part of the unit pattern is adjacent to the triangle in the MD.

The fastening strength, mechanical strength, and thickness of the nonwoven web for a receiving fastener component were measured and evaluated. The results obtained are shown in Table 4.

Comparative Example 1

A nonwoven web for a receiving fastener component was prepared in the same manner as in Example 21 except a web was formed by composite hot-melt spinning via a spun-bonding method using only a propylene-ethylene random copolymer having a melting point of 142° C. and MFR=60 g/10 min. The fastening strength, mechanical strength, and thickness of the resultant nonwoven web for a receiving fastener component were measured and evaluated. The results obtained are shown in Table 4.

Comparative Example 2

Figure 11:
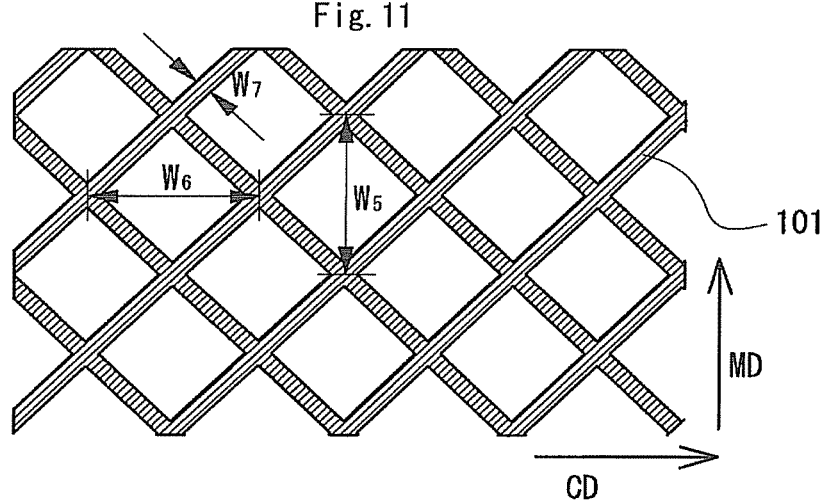
FIGS. 11-13 illustrate engraved patterns of surfaces of embossing rolls used in Comparative Examples 2-4.

A nonwoven web for a receiving fastener component was prepared in the same manner as in Example 21 except that an embossing roll having a surface engraved with the pattern shown in FIG. 11 was employed. The embossing pattern of the nonwoven web for a receiving fastener component contains a diamond pattern disposed in the MD and CD over the web. In the embossed portion 101, a distance between intersections in MD $W_5$=11.1 mm, a distance between intersections in CD $W_6$=11.1 mm, and a line width $W_7$=1 mm, and an embossed area ratio is 24%.

The fastening strength, mechanical strength, and thickness of the resultant receiving fastener component were measured and evaluated. The results obtained are shown in Table 4.

Comparative Example 3

Figure 12:
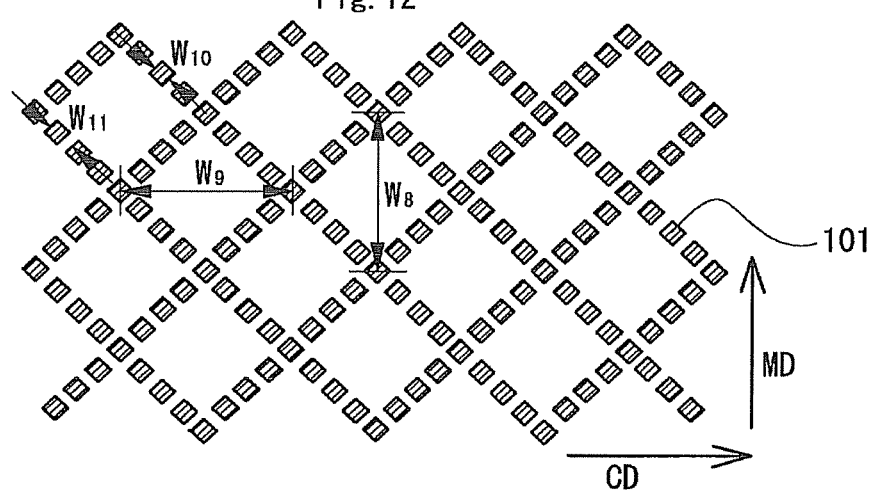

A nonwoven web for a receiving fastener component was prepared in the same manner as in Example 21 except that an embossing roll having a surface engraved with the pattern shown in FIG. 12 was employed. The embossing pattern of the nonwoven web for a receiving fastener component contains a diamond pattern disposed in the MD and CD over the web, and the diamond pattern contains a line containing square dots disposed with a predetermined interval. In the embossed portion 101, a distance between intersections in MD $W_8$=8.5 mm, a distance between intersections in CD $W_9$=8.0 mm, a width of the dot in the line direction $W_{10}$=0.685 mm, a width of the dot in the line direction plus a width of the interval between the dots $W_{11}$=1.46 mm, and an embossed area ratio was 10%.

The fastening strength, mechanical strength, and thickness of the resultant nonwoven web for a receiving fastener component were measured and evaluated. The results obtained are shown in Table 4.

Comparative Example 4

Figure 13:
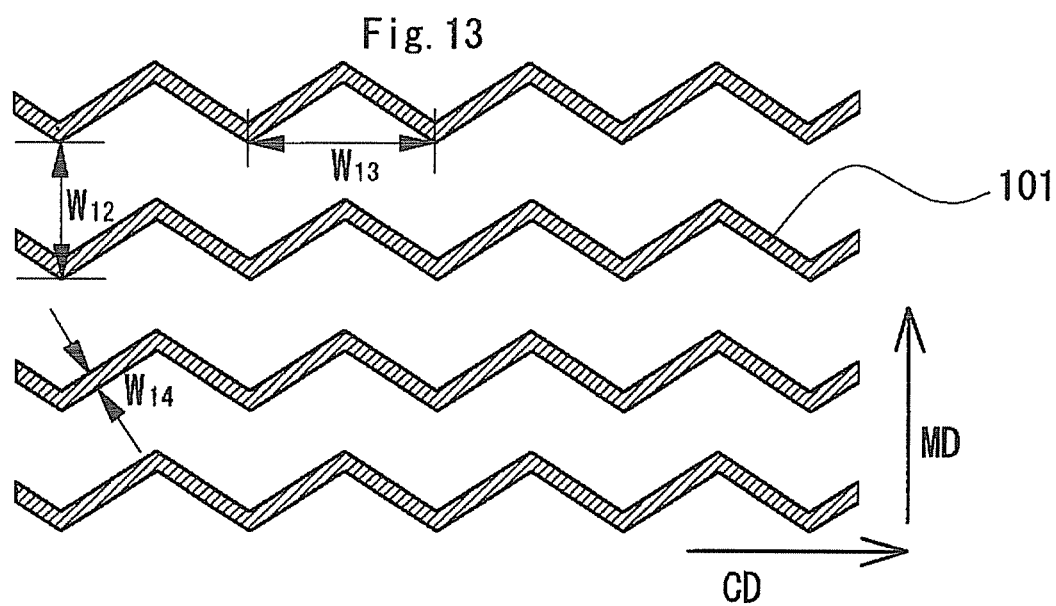

A nonwoven web for a receiving fastener component was prepared in the same manner as in Example 21 except that an embossing roll having a surface engraved with the pattern shown Iin FIG. 13 was employed. The embossing pattern of the nonwoven web for a receiving fastener component contains unit patterns disposed in the MD, the unit pattern containing a relatively even zigzag and being disposed parallel to the CD. In the embossed portion 101, a distance between apexes in the MD (pitch of the unit pattern) $W_{12}$=7 mm, a distance between apexes in the CD $W_{13}$=9 mm, a line width $W_{14}$=1 mm, and an embossed area ratio is 16%.

Furthermore, a triangle formed by adjacent three contact points of the first diagonal line and the second diagonal line in the unit pattern does not contain a part of the unit pattern that is adjacent to the triangle in the MD.

The fastening strength, mechanical strength, and thickness of the nonwoven web for a receiving fastener component were measured and evaluated. The results obtained are shown in Table 4.

conflicts with any meaning or definition of the term in a document incorporated by reference, the meaning or definition assigned to the term in this written document shall govern.

What has been described above includes examples of the subject invention. It is, of course, not possible to describe every conceivable combination of components or methodologies for purposes of describing the subject invention, but one of ordinary skill in the art may recognize that many further combinations and permutations of the subject invention are possible. Accordingly, the subject invention is intended to embrace all such alterations, modifications and variations that fall within the spirit and scope of the appended claims.

Furthermore, to the extent that the term "includes," "involves," and "contain" are used in either the detailed description or the claims, such terms are intended to be inclusive in a manner similar to the term "comprising" as "comprising" is interpreted when employed as a transitional word in a claim.

In addition, the dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

What is claimed is:

1. A receiving component of a fastener including a nonwoven web comprising a composite fiber having crimps,
   the nonwoven web comprising an embossed portion and a non-embossed portion on only one surface of the nonwoven web, the composite fibers in the embossed portion being bonded by thermal compression by an embossing roll, the composite fibers in the non-embossed portion being capable of engaging with a plurality of hooks of an engaging component,
   the embossed portion comprising an embossing pattern that comprises a plurality of zigzag unit patterns disposed in a machine direction, each zigzag unit pattern being spaced from each other, the zigzag unit patterns being continuous and parallel with a cross machine direction of the embossing roll,
   the zigzag unit patterns comprising a plurality of first diagonal lines and a plurality of second diagonal lines that are disposed alternately, the plurality of first diago-

TABLE 4

|  |  | Example 21 | Comp. Example 1 | Comp. Example 2 | Comp. Example 3 | Comp. Example 4 |
|---|---|---|---|---|---|---|
| First propylene polymer | wt. % | 20 | 0 | 20 | 20 | 20 |
| Second propylene polymer | wt. % | 80 | 100 | 80 | 80 | 80 |
| Basis weight. | g/m² | 45 | 45 | 45 | 45 | 45 |
| Embossed area ratio | % | 24 | 24 | 24 | 10 | 16 |
| Embossing pattern |  | FIG. 3B | FIG. 3B | FIG. 11 | FIG. 12 | FIG. 13 |
| Peel strength | N/25 mm | 3.7 | 1.8 | 3.2 | 2.6 | 3 |
| Repeat peel strength | N/25 mm | 3 | n/a | 2.7 | 1.1 | 1.4 |
| Tensile shear strength | N/25 mm | 38 | 14 | 36.9 | 19.3 | 37.2 |
| MD maximum tensile strength | N/25 mm | 42.3 | 49.2 | 45.8 | 32.6 | 40.5 |
| CD maximum tensile strength | N/25 mm | 22.7 | 23.4 | 16.1 | 12.8 | 13.9 |
| Thickness (bulkiness) | µm | 540 | 380 | 510 | 420 | 550 |

All documents cited in the DESCRIPTION are, in relevant part, incorporated herein by reference; the citation of any document is not to be construed as an admission that it is prior art with respect to the subject invention. To the extent that any meaning or definition of a term in this written document nal lines being disposed parallel to each other and respective first diagonal lines being inclined to a first side at a same angle to the machine direction, the second diagonal lines being disposed parallel to each other and respective second diagonal lines being inclined to a second side at a same angle to the machine direction, first diagonal lines and second diagonal lines being continuous and connected alternately at an end portion or an adjacent portion to the end portion of the first diagonal lines and second diagonal lines, a triangle formed by adjacent three contact points of a first diagonal line and a second diagonal line adjacent to the first diagonal line of the zigzag unit pattern being overlapped by a part of another zigzag unit pattern that is adjacent to the triangle in the machine direction, where the three contact points are at a location where the first diagonal line and the adjacent second diagonal line connect and at other ends of the first diagonal line and the adjacent second diagonal line, and the triangle is formed when imaginary lines connect the three contact points to each other, the zigzag unit patterns having a ratio of $W_1/W_2$ of about 0.1 to about 10, wherein $W_1$ is a width between a first apex on a first side and a second apex on a second side of the zigzag unit pattern in the machine direction and $W_2$ is a width between adjacent contact points of a first diagonal line and a second diagonal line in the cross machine direction, the composite fiber having crimps being a side-by-side composite fiber comprising a first propylene polymer and a second propylene polymer, wherein the first and second propylene polymers are arranged to occupy a first area and a second area of a cross section of the composite fiber, respectively, and extend continuously in a longitudinal direction, and each of the first and second propylene polymers forms at least a portion of peripheral surface continuously along the longitudinal direction of the composite fiber, and a melting point of the first propylene polymer measured by differential scanning calorimetry being higher than a melting point of the second propylene polymer by about 15° C. or more, and a weight ratio of the first propylene polymer to the second propylene polymer being from about 50/50 to about 5/95, wherein an area percentage of the embossed portion to a sum of the embossed portion and the non-embossed portion is in a range of about 20% to about 30%, and the nonwoven web is a spunbonded nonwoven web.

2. The receiving component of a fastener of claim 1, wherein $W_1$ is from about 3 to about 50 mm, and $W_3$, which is a distance in the machine direction between adjacent zigzag unit patterns, is from about 1 to about 20 mm.

3. The receiving component of a fastener of claim 1, wherein the zigzag unit pattern comprises first diagonal lines and second diagonal lines continuously connected at end portions of each of the first and second diagonal lines.

4. The receiving component of a fastener of claim 2, wherein the zigzag unit pattern comprises first diagonal lines and second diagonal lines continuously connected at end portions of each of the first and second diagonal lines.

5. The receiving component of a fastener of claim 1, wherein the zigzag unit pattern comprises first diagonal lines and second diagonal lines continuously connected at end portions of either of the first or second diagonal lines, and adjacent portions of the end portions of other diagonal lines.

6. The receiving component of a fastener of claim 2, wherein the zigzag unit pattern comprises first diagonal lines and second diagonal lines continuously connected at end portions of either of the first or second diagonal lines, and adjacent portions of the end portions of other diagonal lines.

7. The receiving component of a fastener of claim 1, wherein the embossed portion comprises the zigzag unit pattern disposed in the machine direction with intervals and a dot pattern disposed between adjacent two zigzag unit patterns and formed by bonding the composite fibers via thermal compression using an embossing roll.

8. The receiving component of a fastener of claim 6, wherein the embossed portion comprises the zigzag unit pattern disposed in the machine direction with intervals and a dot pattern disposed between adjacent two zigzag unit patterns and formed by bonding the composite fibers via thermal compression using an embossing roll.

9. The receiving component of a fastener of claim 1, wherein a ratio of melt flow rate of the second propylene polymer divided by a melt flow rate of the first propylene polymer measured in accordance with ASTM D 1238 is from about 0.8 to about 1.2.

10. The receiving component of a fastener of claim 8, wherein a ratio of melt flow rate of the second propylene polymer divided by a melt flow rate of the first propylene polymer measured in accordance with ASTM D 1238 is from about 0.8 to about 1.2.

11. The receiving component of a fastener of claim 1, wherein the first and second propylene polymers are individually a propylene homopolymer or a propylene/ethylene random copolymer having an ethylene unit content ranging about 0 to about 10 mol % and a melt flow rate ranging about 20 to about 200 g/10 minutes as measured in accordance with ASTM D 1238.

12. The receiving component of a fastener of claim 10, wherein the first and second propylene polymers are individually a propylene homopolymer or a propylene/ethylene random copolymer having an ethylene unit content ranging 0 to about 10 mol % and a melt flow rate ranging about 20 to about 200 g/10 minutes as measured in accordance with ASTM D 1238.

13. The receiving component of a fastener of claim 1, wherein the nonwoven web for a receiving component of a fastener comprises a laminate in which the nonwoven web comprising composite fibers having crimps is laminated as an outermost layer of the laminate and at least one layer is laminated on a backside of the nonwoven web.

14. The receiving component of a fastener of claim 12, wherein the nonwoven web for a receiving component of a fastener comprises a laminate in which the nonwoven web comprising composite fibers having crimps is laminated as an outermost layer of the laminate and at least one layer is laminated on a backside of the nonwoven web.

15. The receiving component of a fastener of claim 1, wherein a second nonwoven web comprising a propylene polymer fiber is laminated on the nonwoven web comprising composite fibers having crimps.

16. The receiving component of a fastener of claim 1, wherein the zigzag unit pattern comprises straight first diagonal lines and straight second diagonal lines.

17. The receiving component of a fastener of claim 1, wherein the zigzag unit pattern comprises extension lines that extend from connected portions of the first and second diagonal lines in a direction parallel to the machine direction.

18. The receiving component of a fastener of claim 1, wherein the zigzag unit pattern comprises extension lines that extend from connected portions of the first and second diagonal lines in a direction parallel to the first diagonal lines or the second diagonal lines.

19. The receiving component of a fastener of claim 1, wherein the zigzag unit pattern comprises extension lines that extend from connected portions of the first and second diagonal lines at an angle in a range from about 60 degrees to about 120 degrees with respect to the machine direction.

20. The receiving component of a fastener of claim 1, wherein a difference in height between the non-embossed portion and the embossed portion is in a range of about 0.1 to about 2 mm.

21. The receiving component of a fastener of claim 1, wherein the area percentage of the embossed portion to the sum of the embossed portion and the non-embossed portion is from 20.7% to about 30%.

22. The receiving component of a fastener of claim 1, wherein the area percentage of the embossed portion to the sum of the embossed portion and the non-embossed portion is from 23% to about 30%.

\* \* \* \* \*